US010711246B2

(12) United States Patent
Keller et al.

(10) Patent No.: US 10,711,246 B2
(45) Date of Patent: Jul. 14, 2020

(54) METHODS AND COMPOSITIONS FOR GENERATING EPICARDIUM CELLS

(71) Applicant: UNIVERSITY HEALTH NETWORK, Toronto, Ontario (CA)

(72) Inventors: Gordon Keller, Toronto (CA); Alec Drake Witty, La Jolla, CA (US); Steven James Kattman, Madison, WI (US)

(73) Assignee: UNIVERSITY HEALTH NETWORK, Toronto, Ontario (CA)

( * ) Notice: Subject to any disclaimer, the term of this patent is extended or adjusted under 35 U.S.C. 154(b) by 235 days.

(21) Appl. No.: 14/915,992

(22) PCT Filed: Sep. 12, 2014

(86) PCT No.: PCT/CA2014/000687
§ 371 (c)(1),
(2) Date: Mar. 2, 2016

(87) PCT Pub. No.: WO2015/035506
PCT Pub. Date: Mar. 19, 2015

(65) Prior Publication Data
US 2016/0215263 A1 Jul. 28, 2016

Related U.S. Application Data

(60) Provisional application No. 61/877,618, filed on Sep. 13, 2013.

(51) Int. Cl.
C12N 5/077 (2010.01)
C12Q 1/6881 (2018.01)
G01N 33/50 (2006.01)

(52) U.S. Cl.
CPC ......... *C12N 5/0657* (2013.01); *C12Q 1/6881* (2013.01); *G01N 33/5023* (2013.01); *G01N 33/5044* (2013.01); *G01N 33/5061* (2013.01); C12N 2501/115 (2013.01); C12N 2501/155 (2013.01); C12N 2501/16 (2013.01); C12N 2501/165 (2013.01); C12N 2501/40 (2013.01); C12N 2506/45 (2013.01); *C12Q 2600/158* (2013.01)

(58) Field of Classification Search
CPC ............ C12N 5/0657; C12N 2501/115; C12N 2501/155; C12N 2501/16; C12N 2501/165; C12N 2501/40; C12N 2506/45; C12Q 1/6881; C12Q 260/158; G01N 33/5023; G01N 33/5044; G01N 33/5061
See application file for complete search history.

(56) References Cited

U.S. PATENT DOCUMENTS 5,843,780 A 12/1998 Thomson
5,945,577 A 8/1999 Stice et al.
5,994,619 A 11/1999 Stice et al.
6,200,806 B1 3/2001 Thomson
6,235,970 B1 5/2001 Stice et al.
7,763,464 B2 7/2010 Xu
(Continued)

FOREIGN PATENT DOCUMENTS

CN 1543500 A 11/2004
JP 2011-517563 T 6/2011
WO 2009/120762 A2 10/2009
(Continued)

OTHER PUBLICATIONS

Smart et al., Nature, 474: 640-644, 2011.*
Malaguti et al., eLife, 2: e01197, 2013.*
Lu et al. PNAS, 103(15): 5688-5693, 2006.*
Hu et al., Development 136: 1443-1452, 2009.*
TGF Beta Pathway accessed from https://www.thermofisher.com/us/en/home/life-science/antibodies/antibodies-learning-center/antibodies-resource-library/cell-signaling-pathways/tgf-beta-pathway.html on May 28, 2018.*
Watabe et al., Cell Research, 19:103-115, 2009.*
MacDonald et al., Dev Cell.; 17(1): 9-26, 2009.*
Partial Supplementary European Search Report in EP Application No. 14844375.7, dated Feb. 3, 2017.
Witty et al., "Generation of the epicardial lineage from human pluripotent stem cells," Nature Biotechnol. vol. 32, No. 10, 2014, pp. 1026-1035.
(Continued)

Primary Examiner — Thaian N. Ton
(74) Attorney, Agent, or Firm — Proskauer Rose LLP

(57) ABSTRACT

Provided are methods and products for obtaining cardiovascular lineage cells from hPSCs. The method for obtaining a cardiomyocyte lineage or an epicardial lineage cell population from human pluripotent stem cells (hPSCs) comprises one or more of the following steps: (a) contacting BMP component primed hPSCs with a cardiovascular mesoderm programming cocktail suitable for inducing the hPSCs to differentiate to a cardiovascular mesoderm cell population under conditions suitable for the programming cocktail to penetrate the hPSCs and culturing the contacted hPSCs for a period of time to generate a KDR+ and PDGFRalpha+ cardiovascular mesoderm cell population; (b) contacting the cardiovascular mesoderm cell population with a cardiovascular progenitor specification cocktail suitable to specify a NKX2-5+ or WT1+ cardiovascular progenitor cell population under conditions suitable for the specification cocktail to penetrate the cardiovascular mesoderm cell population and culturing the contacted cardiovascular mesoderm cell population for a period of time to generate a NKX2-5+ or WT1+ cardiovascular progenitor cell population; and (d) contacting the cardiovascular progenitor cell population with a maturation cocktail under conditions suitable for the maturation cocktail to penetrate the cardiovascular progenitor cell population and culturing the contacted cardiovascular progenitor population for a period of time to produce a cardiovascular population optionally cardiomyocyte lineage cells expressing cardiac troponin T (cTnT) and/or SIRPA and/or epicardial lineage cells expressing WT1.

22 Claims, 17 Drawing Sheets

(56) References Cited

U.S. PATENT DOCUMENTS

2005/0054092 A1 3/2005 Xu et al.
2011/0305672 A1 12/2011 Dalton et al.

FOREIGN PATENT DOCUMENTS

| WO | 2012/024782 A1 | 3/2012 |
| WO | WO/2012024782 A1 | 3/2012 |
| WO | 2013/056072 A1 | 4/2013 |
| WO | WO/2013056072 A1 | 4/2013 |
| WO | WO 2015/035506 | 3/2015 |

OTHER PUBLICATIONS

Yang et al., "Human cardiovascular progenitor cells develop from a KDR+ embryonic-stem-cell-derived population," Nature, vol. 453, 2008, pp. 524-528.
Chen-Leng Cai et al., "A myocardial lineage derives from Tbx18 epicardial cells", Nature, Letters, vol. 454, Jul. 3, 2008, pp. 104-108.
Lei Yang et al., "Human cardiovascular progenitor cells develop from a KDR+ embryonic-stem-cell-derived population", Nature, Letters, vol. 453, May 22, 2008, pp. 524-528.
Anita F. Austin et al., "Primary and Immortalized Mouse Epicardial Cells Undergo Differentiation in Response to TGFβ", Research Article, Developmental Dynamics, vol. 237, pp. 366-376, 2008.
Olivey et al., "Transforming Growth Factor-β Stimulates Epithelial-Mesenchymal Transformation in The Proepicardium" NIH Public Access, Dev Dyn. Jan. 2006; 235(1): 50-59.
Kruithof et al., "BIVIP and FGF regulate the differentiation of multipotential pericardial mesoderm into the myocardian or epicardial lineage", Developmental Biology, 295, Apr. 3, 2006, pp. 507-522.
Van Tuyn et al., "Epicardial Cells of Human Adults Can Undergo an Epithelial-to-Mesenchymal Transition and Obtain Characteristics of Smooth Muscle Cells In Vitro", Stem Cells, 2007;25, pp. 271-278.
Von Gise et al., "VVT1 regulates epicardial epithelial to mesenchymal transition through β-catenin and retinoic acid signaling pathways", Developmental Biology 355, Feb. 4, 2011, pp. 421-431.
Morabito et al., "Positive and Negative Regulation of Epicardiail-Mesenchymal Transformation during Avian Heart Development", Developmental Biology 234, pp. 204-215, (2001).
Supplemental European Search Report of PCT International Application No. PCT/CA2014/000687, dated May 10, 2017.
International Search Report and Written Opinion in corresponding International Application No. PCT/CA2014/000687, dated Jan. 6, 2015.
Burridge et al., "Production of de novo cardiomyocytes; human pluripotent stem cell differentiation and direct reprogramming," Stem Cell, Jan. 6, 2012, vol. 10, pp. 16-28.
Kattman et al., "Stage-specific optimization of activin/nodal and BMP signaling promotes cardiac differentiation of mouse and human pluropitent stem cell lines," Stem Cell, Feb. 4, 2011, vol. 8, pp. 228-240_
Klaus et al., "Wnt/beta-catenin and Bmp signals control distinct sets of transcription factors in cardiac progenitor cells," Proc. Natl. Acad. Sci. U.S.A., Jul. 3, 2012, vol. 109, pp. 10921-10926.
Willems et al., "Small-molecule inhibitors of the Wnt pathway potently promote cardiomyocytes from human embryonic stem cell-derived mesoderm," Circ. Res., Aug. 5, 2011, vol. 109, pp. 360-364.
Steven J. Kattman et al., "Stage-Specific Optimization of Activin/Nodal and BMP Signaling Promotes Cardiac Differentiation of Mouse and Human Pluripotent Stem Cell Lines," Cell Stem Cell, 2011, vol. 8, pp. 228-240.
P.W. Burridge et al., "Production of de novo cardiomyocytes: human pluripotent stem cell differentiation and direct reprogramming," Cell Stem Cell, 2012, vol. 10, pp. 16-28.
Erik Willems et al., "Small-Molecule Inhibitors of the Wnt Pathway Potently Promote Cardiomyocytes From Human Embryonic Stem Cell-Derived Mesoderm," Circulation Research, 2011, vol. 109, pp. 360-364.

L. Yang et al., "Human cardiovascular progenitor cells develop from a KDR+ embryonic-stem-cell-derived population," Nature, 2008, vol. 453, pp. 524-528.
A. F. Austin et al., "Primary and Immortalized Mouse EpicardialCells Undergo Differentiation in Response toTGFβ," Developmental dynamics, 2008, vol. 237, No. 2, pp. 366-376.
H. E. Olivey et al., "Transforming growth factor-β stimulates epithelial—mesenchymal transformation in the proepicardium," Developmental dynamics, 2006, vol. 235, No. 1, pp. 50-59.
B. P. T. Kruithof et al., "BMP and FGF regulate the differentiation of multipotential pericardial mesoderm into the myocardial or epicardial lineage," Developmental biology, 2006, vol. 295, No. 2, pp. 507-522.
Klaus, A. et al. "WNT/Beta-catenin and BMP signals control distinct sets of transcription factors in cardiac progenitor cells", Proc Natl Acad Sci USA., 2012, vol. 109, pp. 10921-10926.
Acharya, A. et al., The bHLH transcription factor Tcf21 is required for lineage-specific EMT of cardiac fibroblast progenitors. Development (Cambridge, England) 139, 2139-2149 (2012).
Bochmann, L. et al. Revealing new mouse epicardial cell markers through transcriptomics. PloS ONE 5(6), e11429 (2010).
Brade, T. et al., Retinoic acid stimulates myocardial expansion by induction of hepatic erythropoietin which activates epicardial Igf2. Development (Cambridge, England) 138, 139-148 (2011).
Bumol, T.F., Marder, P., Dehert, S.V. Borowitz, M.J. & Apelgren, L.D. Characterization of the human tumor and normal tissue reactivity of the KS 1/4 monoclonal antibody. Hybridoma 7, 407-415 (1988).
Cai, et al. A myocardial lineage derives from Tbx18 epicardial cells. Nature 454, 104-108 (2008).
Cheung, C., Bernardo, A.S., Trotter, M.W., Pedersen, R.A. & Sinha, S. Generation of human vascular smooth muscle subtypes provides insight into embryological origin-dependent disease unsusceptability. Nature biotechnology 30, 165-173 (2012).
Christoffels, V.M. et al., Tbx18 and the fate of epicardial progenitors. Nature 458, E8-9; discussion E9-10 (2009).
Compton, L.A., Potash, D.A., Mundell, N.A. & Barnett, J.V. Transforming growth factor-beta induces loss of epithelial character and smoothe muscle cell differentiation in epicardial cells. Development dynamics 235, 82-93 (2006).
Dubois, N.C. et al. SIRPA is a specific cell-surface marker for isolating cardiomyocytes derived from human pluripotent cells. Nature biotechnology 29, 1011-1018 (2012).
El-Mounayri, O. et al., Serum Free differentiation of functional human coronary-like vascular smooth muscle cells from embryonic stem cells. Cardiovascular research 98, 125-135 (2013).
Grieskamp, e al, A. Notch signaling regulates smooth muscle differentiation of epicardium-derived cells. Circulation Research 108, 813-823 (2011).
LaFlamme, M.A. et al. Cardiomyocytes derived from human embryonic stem cells in pro-survival factors enhance function of infarcted rat hearts. Nature biotechnology 25, 1015-1024 (2007).
Li, P. et al. IGF signaling directs ventricular cardiomyocyte proliferation during embryonic heart development. Development (Cambridge, England) 138, 1795-2805 (2011).
Lie-Venema, H. et al., Origin, fate, and function of epicardium-derived cells (EPDCs) in normal and abnormal cardiac development. ScientificWorldJournal 7, 1777-1798 (2007).
Limana, F. Capogrossi, M.C. & Germani, A. The epicardium in cardiac repair: form the stem cell view. Pharmacology & therapeutics 129, 82-96 (2011).
Liu, J. & Stainer, D.Y. Tbx5 and Bmp signaling are essential for preopicardium specification in zebrafish. Circulation research 106, 1818-1828 (2010).
Mahtab, E.A. et al. Cardiac malformations and myocardial abnormalities in pdoplanin knockout mouse embryos: Correlation with abnormal epicardial development. Developmental Dynamics, 237, 847-857 (2008).
Mellgren, A.M. et al, Platelet-derived growth factor receptor beta signaling is required for efficient epicardial cell migration and development of two distinct coronary vascular smooth muscle cell populations. Circulation research 103, 1393-1401 (2008).

(56) References Cited

OTHER PUBLICATIONS

Momburg, F., Moldenhauer, G., Hammerling, G.J. & Moller, P. Immunohistochemical study of the expression of a Mr 34,000 human epithelium-specific surface glycoprotein in normal and malignant tissues. Cancer research 47, 2883-2891 (1987).
Murray C,E. & Keller, G. Differentiation of embryonic stem cells to clinically relevant populations: lessons from embryonic development. Cell 132, 661-680 (2008).
Phillips, M.D., Mukhopadhyay, M., Poscablo, C. & Westphal, H. Dkk1 and Dkk2 regulate epicardial specification during mouse heart development. International journal of cardiology 150, 186-192 (2011).
Smart, N., et al., Thymosin beta-4 is essential for coronary vessel development and promotes neovascularization via adult epicardium. Annals of the new York Academy of Sciences 1112, 171-188 (2007).
Smith, C.L., Baek, S.T., Sung, C.Y. & Tallquist, M.D. Epicardial-derived epithelial-to-mesenchymal transition and fate specification require PDGF receptor signaling. Circular Research 108, e15-26 (2011).
Weeke-Klimp, A. et al. Epicardium-derived cells enhance proliferation, cellular maturation and alignment of cardiomyocytes. Journal of molecular and cellular cardiology, 49, 606-616 (2010).
Yu, P.B. et al. Dorsomorphin inhibits BMP signals required for embryogenesis and iron metabolism. Nature chem. biotechnology, 4, 33-41 (2008).
Zhou, B. et al., Epicardial progenitors contribute to the cardiomyocyte lineage in the developing heart. Nature. 454, 109-113 (2008).
Zhou, B., et al. Adult mouse epicardium modulates myocardial injury by secreting paracrine factors. The Journal of Clinical Investigation 121, 1894-1904 (2011).
Foreign Office Action (original and English translation), Chinese Patent Application No. 201480048299.6, (dated Apr. 3, 2019).
Foreign Office Action (original and English translation), Indian Patent Application No. 201617006461, (dated Apr. 30, 2019).
Foreign Office Action (original and English translation), Israeli Patent Application No. 244,530, (dated Sep. 16, 2018).
Foreign Office Action (original and English translation), Japanese Patent Application No. 2016-541747, (dated Jun. 26, 2018).
Foreign Office Action (original and English translation), Japanese Patent Application No. 2016-541747, (dated May 21, 2019).

* cited by examiner

A

B

BMP4 (10 ng/ml)

No Treatment

Noggin (400 ng/ml)

A Day 15 Epi Pre-Passage

B Day 15+4 Epi Post-Passage

A

Sendai hIPSC WT1+ Differentation Protocol Schematic

B

H7 ESC WT1+ Differenation Protocol Schematic

METHODS AND COMPOSITIONS FOR GENERATING EPICARDIUM CELLS

RELATED APPLICATIONS

This is a Patent Cooperation Treaty Application which claims the benefit of 35 U.S.C. § 119 based on the priority of U.S. Provisional Patent Application No. 61/877,618, filed Sep. 13, 2013 which is incorporated herein by reference in its entirety.

FIELD

The disclosure provides methods and compositions for producing cardiovascular lineage cells from PSCs, including hPSCs, as well as methods and compositions for producing cardiomyocyte and epicardial lineage cell populations.

BACKGROUND

Over the past five years, progress has been made in our ability to direct the differentiation of human embryonic (hESCs) and induced pluripotent stem cells (hiPSCs) (collectively referred to as human pluripotent stem cells; hPSCs) to specific cells types, including those of the cardiovascular lineages[1,2]. This success is largely based on the translation of our understanding of lineage development and tissue formation in model organisms to the hPSC differentiation cultures[1]. With respect to the cardiovascular system, this approach has led to the establishment of differentiation protocols that recapitulate the key stages of development including the formation of a primitive streak (PS)-like population, the induction of cardiovascular mesoderm and the specification of the cardiovascular lineages from this mesoderm[3,4]. Developmental biology has also informed us on key regulatory pathways that control this developmental progression including the requirement for activin A/nodal and BMP4 signaling to generate the PS/mesoderm population and the need to inhibit β-catenin dependent Wnt signaling to specify the mesoderm to a cardiovascular fate[4]. Recent studies have identified surface markers specific for cell populations representing different stages of cardiovascular development. This marker set includes KDR and PDGFRα found on cardiovascular mesoderm[5] and SIRPA present on cardiovascular progenitors and differentiated cardiomyocytes[6]. By monitoring the emergence of the KDR+PDGFRα+ population, it was shown that different hPSC lines require different concentrations of activin A and BMP4 for optimal mesoderm induction and cardiomyocyte development[5].

The epicardial lineage is derived from a structure known as the proepicardial organ (PEO) that develops adjacent to the heart at approximately embryonic stage (E) 9.5 in the mouse[7]. Pro-epicardial cells characterized by the expression of the transcription factors Wilms Tumor 1 (WT1) and TBX18, migrate from the PEO to the early heart tube during the process of looping and rapidly envelope it to form an outer epithelial layer, known as the epicardium. The epicardium is essential for normal heart development and functions to support rapid proliferation of the ventricular cells and the formation of compact zone myocardium. It is also the source of several major cell types of the heart including cardiac fibroblasts, coronary vascular smooth muscle cells and to a lesser extent endothelial cells. These differentiated progeny are referred to as epicardial-derived cells (EPDCs) and are derived through an epithelial-to-mesenchymal transition (EMT) of the epicardium. Lineage tracing studies suggest that the epicardium is also a source of cardiomyocytes[8,9]. However, the interpretation of these studies has been questioned given the uncertainty of the epicardial specificity of the gene used for the tracing experiments[10].

The epicardium produces a number of factors including retinoic acid (RA), fibroblast growth factors (FGFs) and insulin-like growth factors (IGFs), several of which are essential for the transient phase of ventricular myocyte proliferation necessary for the formation of compact zone myocardium. Recent studies have shown that IGF2 is the critical epicardium-derived factor that promotes ventricular proliferation[11] and that RA mediates this function indirectly through activation of erythropoietin (EPO) in the liver, which in turn induces IGF2 in the epicardium[12]. Evidence also exists for myocardial regulation of the epicardium through the activity of thymosin β4 (Tβ4), a G-actin monomer binding protein[13]. Tβ4 is produced by the developing myocardium and is required for proper epicardial development and integrity.

While the normal adult epicardium does not express WT1, TBX18 or RALDH2[14], injury such as myocardial infarction will lead to the upregulation of this 'fetal' gene program, as well as to proliferation of cells within the population and the reactivation of EMT. Injection of Tβ4 during infarction enhances these changes and prevents myocardial death, likely through the production of paracrine factors from the activated epicardial cells[14,15]. Lineage-tracing studies in the adult suggest that this activated epicardium has some capacity to generate new cardiomyocytes and that this cardiogenic potential is augmented by priming of the pre-infarcted heart with Tβ4[15]. As with the fetal studies, however, this concept is controversial, as recent studies failed to demonstrate any contribution of the epicardium to the myocardium of the infarcted, Tβ4-treated heart[14].

In vitro studies have shown that epicardial cells in explant cultures will undergo EMT and give rise to EPDCs in response to Notch[16], TGFβ[17-19] and PDGFBB[20] or Tβ4[15]. Epicardial cells from infarcted animals primed with Tβ4 in vivo differentiate to cells that express cardiomyocyte markers in explant cultures[15].

Although these advances have enabled the efficient and scalable derivation of cardiomyocytes from hPSCs, these differentiated populations are not optimal for many applications, as they contain immature cells and the proportion of different cardiac lineage cells including myocardial and epicardial within them is not well defined. To realize the potential of hPSCs in cardiovascular research and therapeutic applications, it will likely be necessary to develop culture systems and engineered tissues that more accurately represent the human heart.

SUMMARY

An aspect includes a method of obtaining a cardiovascular lineage cell population, optionally cardiomyocyte lineage cell population or an epicardial lineage cell population from human pluripotent stem cells (hPSCs) comprising the steps: (a) contacting BMP component primed hPSCs with a cardiovascular mesoderm programming cocktail suitable for inducing the hPSCs to differentiate to a cardiovascular mesoderm cell population under conditions suitable for the programming cocktail to penetrate the hPSCs and culturing the contacted hPSCs for a period of time to generate a KDR+ and PDGFRα+ cardiovascular mesoderm cell population; (b) contacting the cardiovascular mesoderm cell population with a cardiovascular progenitor specification cocktail suitable to specify a NKX2-5+ or WT1+ cardiovascular progenitor cell population under conditions suitable for the specification cocktail to penetrate the cardiovascular mesoderm cell population and culturing the contacted cardiovascular mesoderm cell population for a period of time to generate a NKX2-5+ or WT1+ cardiovascular progenitor cell population; and (d) contacting the cardiovascular progenitor cell population with a maturation cocktail under conditions suitable for the maturation cocktail to penetrate the cardiovascular progenitor cell population and culturing the contacted cardiovascular progenitor population for a period of time to produce a cardiovascular lineage population optionally a cardiomyocyte lineage cell population expressing cardiac troponin T (cTnT) and/or SIRPA and/or an epicardial lineage cell population optionally expressing WT1 and/or comprising epicardial derived cells (EPDCs).

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which.

(a) The total proportion of actively cycling cells in EMT-induced cultures was measured for the indicated treatments. Treatment with TGFβ+bFGF generated populations with the largest proportion of actively cycling cells in response to agonists. Bars represent standard error of the mean; N=3/group; *P<0.05, **P<0.01 compared by one-way ANOVA with Tukey post hoc test.
(b) The frequency of calcium cycles in actively cycling cells in the conditions as indicated at baseline and after NE and PE addition. Stacked bars represent the contribution to frequency of calcium cycling during baseline recording (hatched lines), and after NE (white) or PE (black) treatment.
(c) The amplitude of calcium transients after NE and PE addition in the EMT induced cultures. No Treatment NE N=6 cells, PE N=4 cells; TGFβ NE N=6 cells, PE N=12 cells; TGFβ+bFGF NE N=13 cells, PE N=25 cells. *P<0.05 compared by one-way ANOVA with Tukey post hoc test.
(d) The duration of calcium transients after NE and PE addition in the EMT induced cultures. No Treatment NE N=6 cells, PE N=4 cells; TGFβNE N=6 cells, PE N=12 cells; TGFβ+bFGF NE N=13 cells, PE N=25 cells. **P<0.01 compared by one-way ANOVA with Tukey post hoc test.

Figure 16:
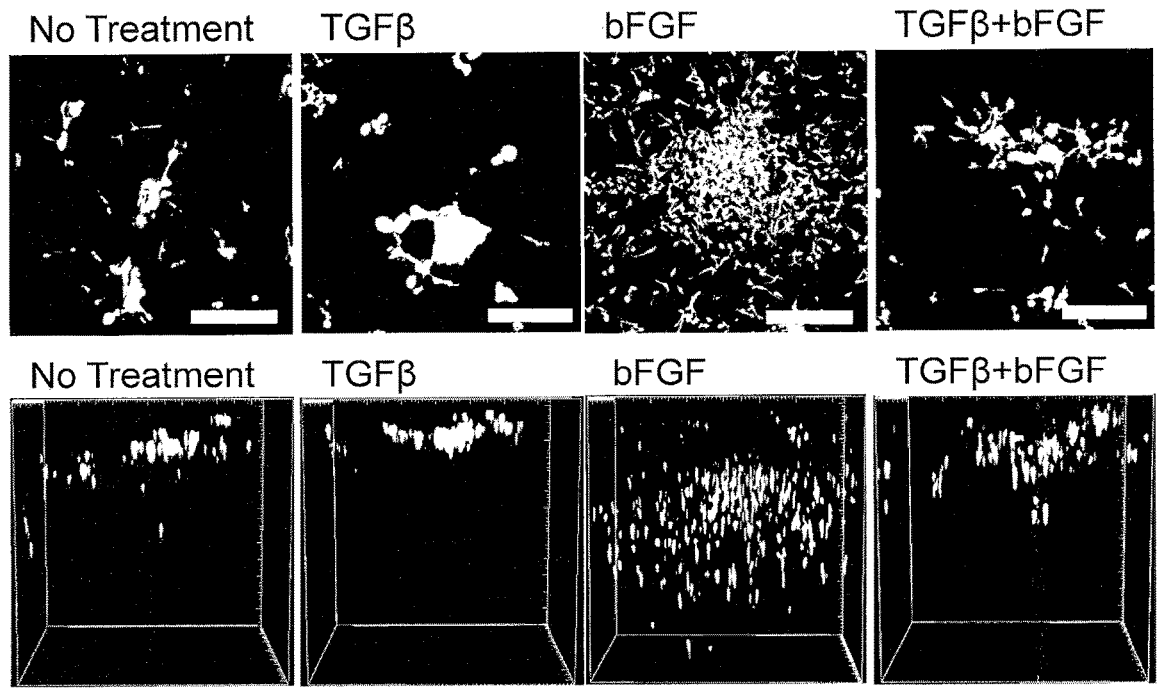
Figure 16:
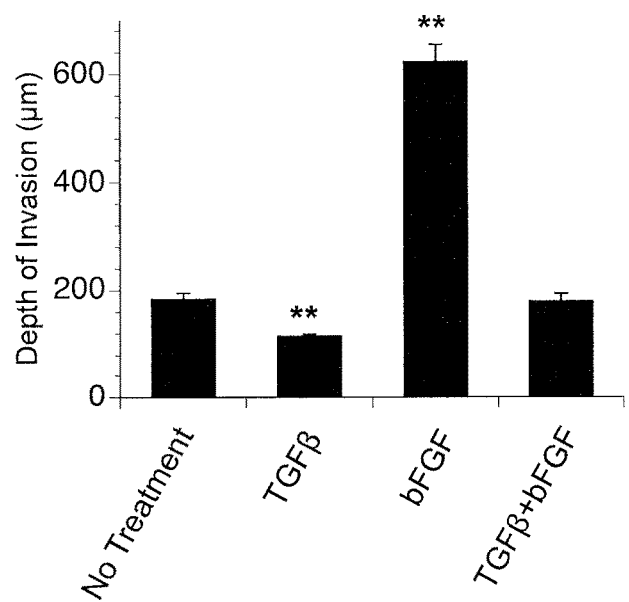

FIG. 16. hESC epicardial-derived fibroblast-like cells invade 3D gels.
(a) Representative fields of view in the XY plane (top view) and 3D reconstruction (side view) of the matrigel invasion assay on D8 after EMT induction.
(b) Maximum matrigel invasion depth on D8 following EMT initiation. Bars represent standard error of the mean of the values from three independent experiments (N=3); **P≤0.01 compared to non-treated controls as analyzed by Student's T-test.

Figure 17:
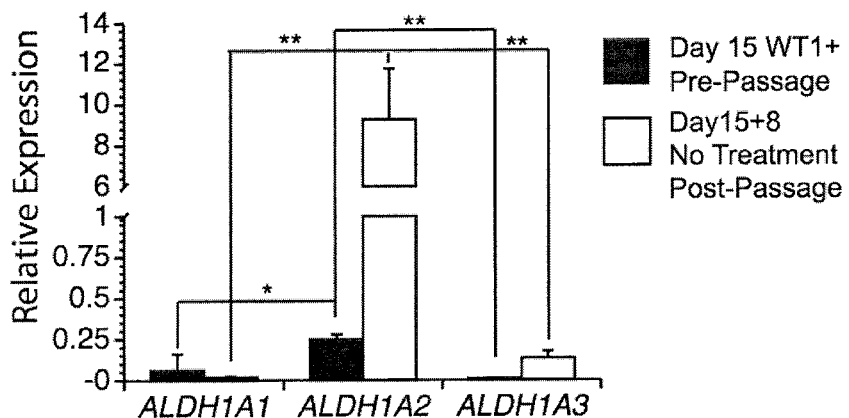
Figure 17:
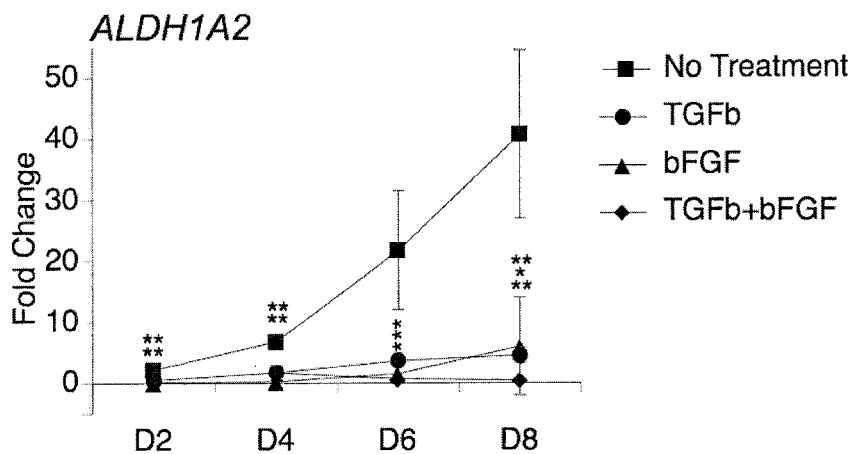
Figure 17:
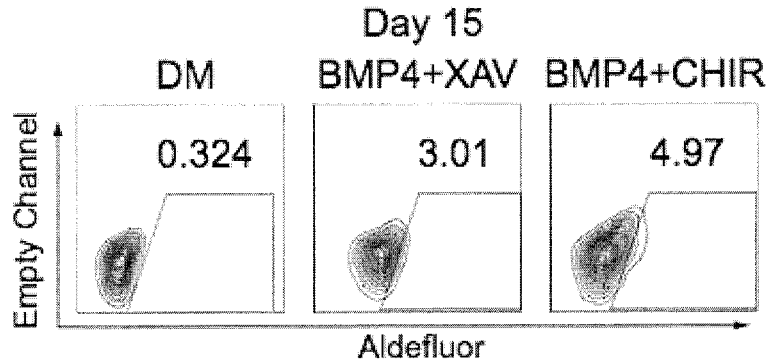
Figure 17:
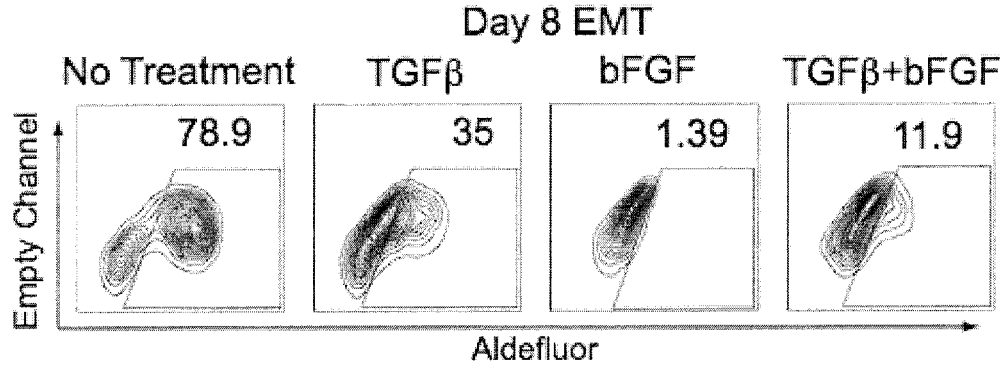

FIG. 17. WT1$^+$ epicardial cells upregulate ALDH1A2 expression and display aldehyde dehydrogenase activity following passage. (a) qRT-PCR-based expression analyses of ALDH1A1, ALDH1A2 and ALDH1A3 in D15 WT$^+$ epicardial cultures and Day 15+8 post-passage non-treated epicardial cultures. Values are relative to the housekeeping gene TBP. Error bars represent standard deviation from the mean of the values from three independent experiments (N=3); *P≤0.05, **P≤0.01 compared to ALDH1A2 expression levels. (b) qRT-PCR-based expression analyses of ALDH1A2 on days 2, 4, 6 and 8 following the initiation of EMT. Values are expressed as fold change to experiment-matched pre-passaged day 15 WT1$^+$ epicardial cultures. Error bars represent standard deviation from the mean of the values from three independent experiments (N=3); *P≤0.05, **P≤0.01 compared to no treatment control cultures. (c) Flow cytometric analyses of Aldefluor on day 15 populations generated from cells treated from days 4 to 6 with DM (non-cardiac, non-epicardial), BMP4+XAV (cardiomyocytes) or BMP4+CHIR (WT1$^+$ epicardial cells). (d) Flow cytometry analyses of Aldefluor on WT1$^+$ epicardium-derived cultures 8 days following the initiation of EMT with the indicated treatments.

Figure 18:
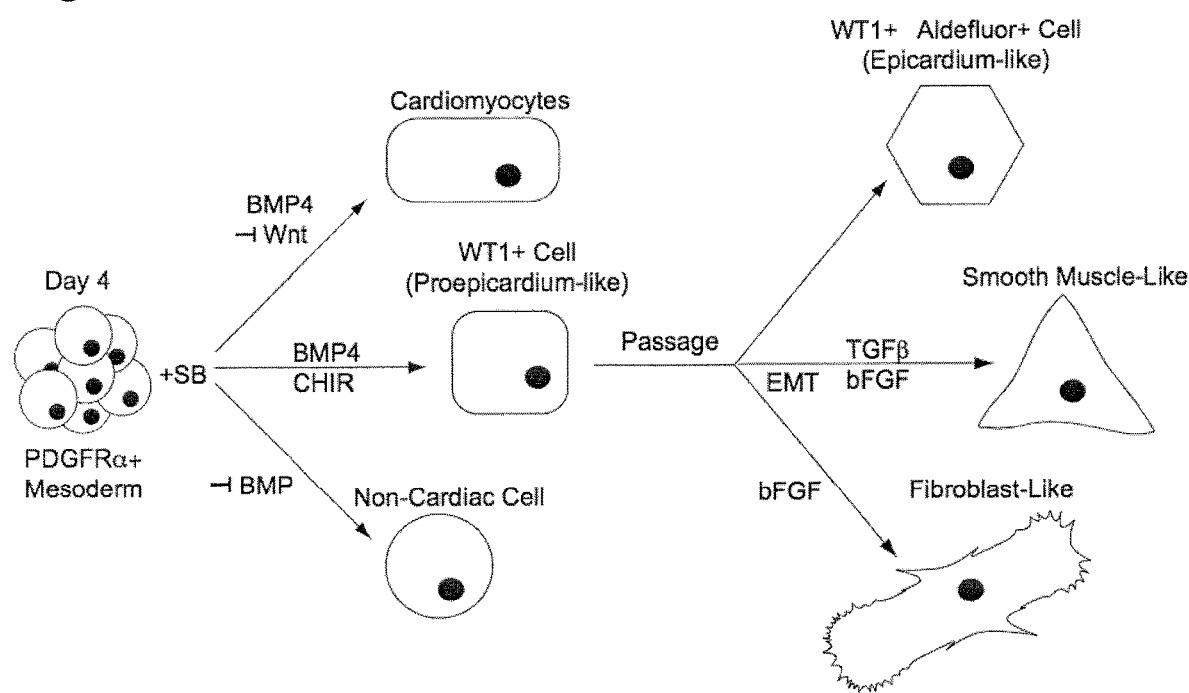

FIG. 18. Differentiation scheme showing cardiomyocyte, epicardium, and EPDC development from hPSC-derived mesoderm.

DETAILED DESCRIPTION OF THE DISCLOSURE

I. Definitions

The term "activin component" as used herein means one or more components, or a composition comprising said component(s), optionally a culture medium comprising a molecule that activates nodal signal transduction, optionally Activin A activity such as Activin A and/or nodal.

The term "activin" or "ActA" as used herein refers to "Activin A", (for example Gene ID: 3624), for example human activinA, as well as active conjugates and fragments thereof, optionally including naturally occurring active conjugates and fragments, that can for example activate nodal signal transduction as well as active conjugates and fragments thereof, including naturally occurring active conjugates and fragments.

The term "activin/nodal inhibitor" and/or "activin/nodal/TGF-βR inhibitor" as used herein means any molecule that inhibits signal of the activin/nodal pathway and particularly any molecule that inhibits receptors ALK4, ALK7 and/or TGF-βRI, including but not limited to SB431542 (Sigma Aldrich) A83-01 (Tocris, 2929), D 4476, GW 788388, LY 364947, RepSox, SB 505124, SB 525334 (Sigma Aldrich), and SD 208.

The term "wnt inhibitor" as used herein means any agent, including any compound and/or protein that inhibits wnt signaling, including but not limited to wnt antagonists that bind either to the Wnt ligand itself, or to Wnt receptors, such as Dickkopf (Dkk) proteins, Wnt Inhibitory Factor-1 (WIF-1), and secreted Frizzled-Related Proteins (sFRPs), as well as wnt inverse agonists (e.g. an agent that binds to the same receptor as an agonist but induces a pharmacological response opposite to that of an agonist). Examples of Wnt inhibitors include XAV939, IWP 2, an inhibitor of wnt processing, and iCRT14, which is a potent inhibitor of β-catenin-responsive transcription (CRT), both of which are available from Tocris Bioscience, as well as combinations thereof.

The term "wnt component" as used herein means any molecule that activates wnt/beta-catenin receptor signaling in a cardiovascular cell and includes for example Wnt3a and as well as GSK3 selective inhibitors such as CHIR99021 (Stemolecule™ CHIR99021 Stemgent), 6-Bromolndirubin-3'-Oxime (BIO) (Cayman Chemical (cat:13123)), or Stemolecule™ BIO from Stemgent (cat:04003). CHIR99021 is a selective inhibitor of GSK3. The GSK3 selective inhibitors contemplated are for example selective inhibitors for GSK-3a/β in the Wnt signaling pathway.

The term "FGF component" as used herein means a molecule such as a cytokine, including for example FGF, or a small molecule, that activates a FGF signalling pathway, e.g. binds and activates a FGF receptor. The term "FGF" as used herein refers to any fibroblast growth factor, for example human FGF1 (Gene ID: 2246), FGF2 (also known as bFGF; Gene ID: 2247), FGF3 (Gene ID: 2248), FGF4 (Gene ID: 2249), FGF5 (Gene ID: 2250), FGF6 (Gene ID: 2251), FGF7 (Gene ID: 2252), FGF8 (Gene ID: 2253), FGF9 (Gene ID: 2254) and FGF10 (Gene ID: 2255) optionally including active conjugates and fragments thereof, including naturally occurring active conjugates and fragments. In certain embodiments, FGF is bFGF, FGF10, FGF4 and/or FGF2.

The term "BMP component" as used herein means any molecule optionally any BMP or growth and differentiation factor (GDF) that activates the receptor for BMP4, including for example BMP4 and BMP2, The term "BMP inhibitor" as used herein means any inhibitor of BMP signaling and includes for example a type 1 BMP receptor inhibitor, BMP ligands and/or soluble BMP receptors. Optionally selected from dorsomorphin (DM), noggin, Chordin, LDN-193189, soluble BMPR1a, and/or soluble BMPR1b.

The term "BMP4" (for example Gene ID: 652) as used herein refers to Bone Morphogenetic Protein 4, for example human BMP4, as well as active conjugates and fragments thereof, optionally including naturally occurring active conjugates and fragments, that can for example activate BMP4 receptor signaling.

The term "BMP component primed hPSCs" as used herein means hPSCs that have been contacted with a BMP component for at least 12 hours, preferably at least 24 hours or more preferably at least 48 hours. Typically these cells are in embryoid bodies or monolayer cultures.

The term "cardiovascular lineage cell" refers to a cell that expresses a cardiovascular mesoderm, cardiomyocyte or an epicardial gene expression pattern, for example expresses KDR, PDGFRα, NK2 homeobox 5 (NKX2-5), cardiac troponin T (cTnT), signal-regulatory protein alpha (SIRPA) or Wilms Tumour 1 (WT1) and is primed or has the capacity to differentiate into a cardiomyocyte lineage cell and/or an epicardial lineage cell or an epicardial derived cell (EPDC) such as a vascular smooth muscle like cell or a fibroblast like cell as described herein.

The term "cardiovascular mesoderm programming cocktail" as used herein is a combination comprising a BMP component and an activin component and optionally a FGF component and the cardiovascular mesoderm programming cocktail is contacted with the hPSCs for about 3 to about 5 days.

The term "cardiovascular progenitor specification cocktail" as used herein means a one or more components, a composition comprising said component(s), for specifying a NKX2-5+ or WT1+ cardiovascular progenitor cell population for example a cardiomyocyte promoting component for specifying a NKX2-5+ cardiomyocyte lineage progenitor cell population or a epicardial promoting component for specifying a WT1+ epicardial lineage progenitor cell population.

The term "cardiomyocyte promoting component" as used herein means one or more components or a composition comprising said component(s), said one or more components, comprising: 1) a combination of a Wnt inhibitor optionally selected from, DKK1, XAV939 and IWP2 and a BMP component, optionally wherein the BMP component is BMP4 at a concentration of at least 0.01 ng/mL, at least 0.05 ng/mL, at least 0.1 ng/mL, at least 0.5 ng/mL, at least 1.25 ng/mL, at least 2.5 ng/mL, at least 5 ng/mL, but less than 10 ng/ml, or less than 15 ng/mL or preferably about 0.5 ng/mL; or 2) a BMP inhibitor, such as noggin or dorsomorphin, for example noggin at a concentration of less than 200 ng/mL, less than 150 ng/mL, less than 100 ng/mL, less than 50 ng/mL, or less than 25 ng/mL and/or greater than 12.5 ng/mL; 3) a Wnt inhibitor, for example wherein there is sufficient endogenous BMP4 produced and/or 4) a cardiomyocyte lineage concentration of a BMP component, optionally BMP4 for example wherein the BMP4 is at a concentration of less than 0.63 ng/mL, less than 0.5 ng/mL, less than 0.4 ng/mL, or less than 0.3 ng/mL. The effective concentration and/or combination can be determined by monitoring and optimizing for NKX2-5 expression and/or TNNT2/cTnT expression.

The term "epicardial lineage promoting component" as used herein means one or more components or a composition comprising said component(s), the one or more components comprising an epicardial lineage promoting concentration of a BMP component, optionally BMP4, and optionally a Wnt component. Optionally, the BMP4 is at a concentration of at least 1.25 ng/mL, at least 2.5 ng/mL, at least 5 ng/mL or at least 10 ng/mL and/or the Wnt component is CHIR99021. The effective concentration and/or combination can be determined by monitoring and optimizing for WT1 expression, basonuclin 1 (BNC1) expression, annexin A8 (ANXA8) expression and/or T-box 18 (TBX18) expression.

The term "a cardiomyocyte lineage cell" as used herein refers to a cell that is NKX2-5+ and which can differentiate to a cardiomyocyte, for example using a method described herein.

The term "an epicardial lineage cell" as used herein, refers to a cell that is WT1+ and which can differentiate to an epicardial cell, for example using a method described herein and/or an epicardial derived cells (EPDC).

The term "culturing" as used herein includes any in vitro method of maintaining and/or propagating a population of cells, including monolayer, bead, flask, or 3D cultures, optionally where ambient conditions are controlled as in an incubator and optionally involving passaging of cells.

The term "epithelial-to-mesenchymal transition (EMT) cocktail" as used herein means one or more components or a composition comprising said component(s) for inducing EMT, the one or more components including a TGFβ component such as TGFβ or a combination comprising a TGFβ component and an FGF component such as bFGF.

The term "TGFβ component" or as used herein a component or composition comprising said component that promotes TGFβ signaling and includes for example TGFβ1, TGFβ2 and/or TGFβ3.

A "KDR+ cell" as used herein means a cell exhibiting "kinase-insert domain-containing receptor" (KDR) cell surface expression and a "KDR+ cell population" means a population of cells, wherein at least 50%, at least 60%, at least 70%, at least 80%, at least 90% or at least 95% or more of the cells exhibit KDR cell surface expression.

The term "PDGFRα+ cell" as used herein means a cell exhibiting "platelet derived growth factor receptor a" cell surface expression and a PDGFRα+ cell population means a population of cells, wherein at least 50%, at least 60%, at least 70%, at least 80%, at least 90% or at least 95% or more of the cells exhibit PDGFRα cell surface expression.

The term "concentration" means diluted concentration in the cell culture medium.

As used herein the term "purified population" with respect to a population of cells as used herein refers to a population of cells that has been removed and separated (e.g. isolated) from a mixed or heterogeneous population of cells and/or other components such as culture medium. In some embodiments, a purified population is a substantially pure population of cells as compared to the heterogeneous population from which the cells were isolated or enriched from.

The term "substantially pure", with respect to a particular cell population, refers to a population of cells that is at least about 65%, preferably at least about 75%, at least about 85%, more preferably at least about 90%, and most preferably at least about 95% pure, with respect to the cells making up a total cell population. Similarly, with regard to a "substantially pure" population of for example WT1+ cells, refers to a population of cells that contain fewer than about 30%, fewer than about 20%, more preferably fewer than about 15%, 10%, 8%, 7%, most preferably fewer than about 5%, 4%, 3%, 2%, 1%, or less than 1%, of cells that are not WT1+.

The term "subject" as used herein includes all members of the animal kingdom including mammals, and suitably refers to humans.

The terms "treat", "treating", "treatment", etc., as applied to a cell, include subjecting the cell to any kind of process or condition or performing any kind of manipulation or procedure on the cell. As applied to a subject, the terms refer to providing medical or surgical attention, care, or management to an individual.

The term "treatment" as used herein as applied to a subject, refers to an approach aimed at obtaining beneficial or desired results, including clinical results and includes medical procedures and applications including for example pharmaceutical interventions, surgery, radiotherapy and naturopathic interventions as well as test treatments for treating cancer. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, the terms "administering," "introducing" and "transplanting" are used interchangeably in the context of delivering cells into a subject, by a method or route which results in at least partial localization of the introduced cells at a desired site.

The term "contacting" is intended to include incubating the component(s) and the cell together in vitro (e.g., adding the compound to cells in culture) and the step of contacting can be conducted in any suitable manner. For example the cells may be treated in adherent culture, or in suspension culture, 3D culture, or where the cells are cultured on beads, the cocktail components can be added temporally substantially simultaneously or sequentially (e.g. within 1 hour from an addition of a first component). The cells can also be contacted with another agent such as a growth factor or other differentiation agent or environments to stabilize the cells, or to differentiate the cells further and include culturing the cells under conditions known in the art for example for culturing the pluripotent (and/or differentiated) population for example as further described in the Examples.

The term "cell culture medium" (also referred to herein as a "culture medium" or "medium") as referred to herein is a medium for culturing cells containing nutrients that maintain cell viability and support proliferation and optionally differentiation. The cell culture medium may contain any of the following in an appropriate combination: salt(s), buffer(s), amino acids, glucose or other sugar(s), antibiotics, serum or serum replacement, and other components such as peptide growth factors, vitamins etc. Cell culture media ordinarily used for particular cell types are known to those skilled in the art.

The term "pluripotent stem cell" as used herein refers to a cell with the capacity, under different conditions, to differentiate to more than one differentiated cell type, and for example the capacity to differentiate to cell types characteristic of the three germ cell layers, and includes embryonic stem cells and induced pluripotent stem cells. Pluripotent cells are characterized by their ability to differentiate to more than one cell type using, for example, a nude mouse teratoma formation assay. Pluripotency is also evidenced by the expression of embryonic stem (ES) cell marker. As used herein, pluripotent stems can include cell lines including induced pluripotent stem cells (iPSC) and embryonic stem cells (ESC). In an embodiment, the pluripotent stem cells are not human embryonic stem cells.

As used herein, the terms "iPSC" and "induced pluripotent stem cell" are used interchangeably and refers to a pluripotent stem cell artificially derived (e.g., induced or by complete reversal) from a non-pluripotent cell, typically an adult somatic cell, for example, by inducing expression of one or more genes (including POU4F1/OCT4 (Gene ID; 5460) in combination with, but not restricted to, SOX2 (Gene ID; 6657), KLF4 (Gene ID; 9314), cMYC (Gene ID; 4609), NANOG (Gene ID; 79923), LIN28/LIN28A (Gene ID; 79727)).

The term "embryonic stem cell" is used to refer to the pluripotent stem cells of the inner cell mass of the embryonic blastocyst (see, for example, U.S. Pat. Nos. 5,843,780, 6,200,806). Such cells can also be obtained from the inner cell mass of blastocysts derived from somatic cell nuclear transfer (see, for example, U.S. Pat. Nos. 5,945,577, 5,994, 619, 6,235,970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "expression" refers to the cellular processes involved in producing RNA and proteins and as appropriate, secreting proteins, and cell surface expression, including where applicable, but not limited to, for example, transcription, translation, folding, modification and processing. "Expression products" include RNA transcribed from a gene and polypeptides obtained by translation of mRNA transcribed from a gene.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Methods and Products

Described herein are methods for producing cardiovascular lineage cells including cardiomyocyte lineage cells, epicardial lineage cells and epicardial derived cells. Components and conditions for specifying these cell types as well as markers for monitoring emergence of these cell types are described.

Accordingly, an aspect includes a method of obtaining a cardiovascular lineage cell population, optionally cardiomyocyte lineage cell population or an epicardial lineage cell population from pluripotent stem cells (PSCs) optionally human PSCs (hPSCs) comprising the steps: (a) contacting BMP component primed hPSCs with a cardiovascular mesoderm programming cocktail suitable for inducing the hPSCs to differentiate to a cardiovascular mesoderm cell population under conditions suitable for the programming cocktail to penetrate the hPSCs and culturing the contacted hPSCs for a period of time to generate a KDR+ and PDGFRα+ cardiovascular mesoderm cell population; (b) contacting the cardiovascular mesoderm cell population with a cardiovascular progenitor specification cocktail suitable to specify a NKX2-5+ or WT1+ cardiovascular progenitor cell population under conditions suitable for the specification cocktail to penetrate the cardiovascular mesoderm cell population and culturing the contacted cardiovascular mesoderm cell population for a period of time to generate a NKX2-5+ or WT1+ cardiovascular progenitor cell population; and (c) contacting the cardiovascular progenitor cell population with a maturation cocktail under conditions suitable for the maturation cocktail to penetrate the cardiovascular progenitor cell population and culturing the contacted cardiovascular progenitor population for a period of time to produce a cardiovascular lineage population optionally cardiomyocyte lineage cells expressing cardiac troponin T (cTnT) and/or SIRPA and/or an epicardial lineage cell population optionally expressing WT1 and/or comprising EPDCs.

KDR and PDGFRα can be used to monitor development of a cardiovascular mesoderm cell population. The expression of KDR can be monitored using an antibody specific for KDR and/or the expression of PDGFRα can be monitoring using an antibody specific for PDGFRα. As both are cell surface expressed, KDR and PDGFRα expression can be monitored by measuring cell surface expression. For example, the expression of KDR and PDGFRα can be monitored using flow cytometry.

In an embodiment, the BMP component primed hPSCs are prepared by contacting the hPSCs with BMP component for about 1 to about 2 days, optionally wherein the BMP component is BMP4 and/or BMP2.

In an embodiment, the cardiovascular mesoderm programming cocktail comprises a BMP component and an activin component and optionally a FGF component and the cardiovascular mesoderm programming cocktail is contacted with the hPSCs for about 3 to about 5 days.

In an embodiment, the FGF component comprises bFGF.

In an embodiment, the BMP component comprises BMP4 and/or BMP2.

In an embodiment, the activin component comprises Activin A.

Concentrations of activin component and BMP component can be optimized as described.[5]

In an embodiment, the PSCs are comprised in embryoid bodies.

Using for example steps a) and b) above, it is demonstrated herein that a NKX2-5+ or WT1+ cardiovascular progenitor cell population can be obtained.

Accordingly a further aspect includes a method for obtaining a NKX2-5+ or WT1+ cardiovascular progenitor cell population from PSCs, optionally hPSCs, comprising the steps: (a) obtaining a KDR+ and PDGFRα+ cardiovascular mesoderm cell population from hPSCs optionally as described above; (b) contacting the KDR+ and PDGFRα+ cardiovascular mesoderm cell population with a cardiovascular progenitor specification cocktail under conditions suitable for the specification cocktail to penetrate the cardiovascular mesoderm cell population and culturing the contacted cardiovascular mesoderm cell population for a period of time sufficient to generate a NKX2-5+ or WT1+ cardiovascular progenitor cell population.

In an embodiment, the KDR+ and PDGFRα+ cardiovascular mesoderm cell population is dissociated prior to contacting with the cardiovascular progenitor specification cocktail.

In some embodiments, the KDR+ PDGFRα+ expressing cells are purified before contacting with the cardiovascular progenitor specification cocktail.

In another embodiment, the cardiovascular mesoderm cell population is contacted with the cardiovascular progenitor specification cocktail for at least 12 hours to about 48 hours, or any amount of time between 12 and 48 hours.

In an embodiment, the cardiovascular progenitor specification cocktail comprises a cardiomyocyte lineage promoting component, wherein the cardiomyocyte promoting component is in a suitable concentration for promoting cardiomyocyte development and specifies a NKX2-5+ cardiovascular progenitor population.

In an embodiment, the cardiomyocyte promoting component comprises a BMP inhibitor, for example for use with cardiovascular mesoderm cell population endogenously expressing a level of BMP that inhibits cardiomyocyte specification.

In an embodiment, the cardiomyocyte promoting component comprises noggin at a concentration of less than 200 ng/mL, less than 150 ng/mL, less than 100 ng/mL, less than 50 ng/mL, or less than 25 ng/mL and/or greater than 12.5 ng/mL.

In another embodiment, the cardiomyocyte promoting component is dorsomorphin at a concentration of less than 1 μM, less than 0.5 μM, less than 0.25 μM, or less than 0.1 μM.

In another embodiment, the cardiomyocyte promoting component is BMP4 at a concentration of less than 0.63 ng/mL, less than 0.5 ng/mL, less than 0.4 ng/mL, or less than 0.3 ng/mL.

In another embodiment, the cardiovascular progenitor specification cocktail comprises: 1) a combination of a Wnt inhibitor optionally selected from, DKK1, XAV939 and IWP2 and a BMP component, optionally wherein the BMP component is BMP4 at a concentration of at least 0.01 ng/mL, at least 0.05 ng/mL, at least 0.1 ng/mL, at least 0.5 ng/mL, at least 1.25 ng/mL, at least 2.5 ng/mL, at least 5 ng/mL, but less than 10 ng/ml, or less than 15 ng/mL or preferably about 0.5 ng/mL; or 2) a BMP inhibitor, such as noggin or dorsomorphin, for example noggin at a concentration of less than 200 ng/mL, less than 150 ng/mL, less than 100 ng/mL, less than 50 ng/mL, less than 25 ng/mL or greater than 12.5 ng/mL; 3) a Wnt inhibitor, for example wherein there is sufficient endogenous BMP4 produced; and/or 4) a cardiomyocyte lineage concentration of a BMP component, optionally BMP4 for example wherein the BMP4 is at a concentration of less than 0.63 ng/mL, less than 0.5 ng/mL, less than 0.4 ng/mL, or less than 0.3 ng/mL. The effective concentration and/or combination can be determined by monitoring and optimizing for NKX2-5 expression and/or TNNT2/cTnT expression.

A Wnt inhibitor can be used without BMP to induce cardiomyocyte specification for example when the mesoderm population of cells produces sufficient endogenous BMP component.

A BMP component in a concentration that promotes cardiomyocyte specification can be used for example when the mesoderm population of cells produces insufficient endogenous BMP component.

The level of an endogenous component that is secreted, such as BMP4 or BMP2 can measured by ELISA or other quantitative immunoassays or quantitative RT-PCR.

In another embodiment, the KDR+ PDGFRα+ cardiovascular mesoderm population and/or the NKX2-5+ cardiovascular progenitor population is purified/isolated.

In another embodiment, the NKX2-5+ cardiovascular progenitor cell population is further contacted with a maturation cocktail optionally comprising a VEGF component. The maturation cocktail can be culture medium suitable for the cell type and/or include additional components.

A further aspect includes a method for producing cardiac troponin T+ (cTnT) cardiomyocyte lineage cell population comprising: (a) obtaining a NKX2-5+ cardiovascular progenitor population according to the method of any one of claims 1 to 16; (b) contacting the cardiovascular progenitor cell population with a maturation cocktail comprising a VEGF component under conditions suitable for the maturation cocktail to penetrate the cardiovascular progenitor cell population; and (b) culturing the contacted cardiovascular progenitor population for a period of time sufficient to produce cardiomyocytes expressing cardiac troponin T (cTnT).

In an embodiment, the NKX2-5+ cardiovascular progenitor population is contacted with the maturation cocktail for 4 or more days, for example at least about 4, optionally about 5, about 9, about 15 or about 20 days, optionally until mature contracting cardiomyocytes are produced. The cells can be kept in culture to mature until the desired cell population is obtained.

A further aspect is a method of producing a WT1+ epicardial lineage cell population, comprising the steps: (a) obtaining a KDR+ and PDGFRα+ cardiovascular mesoderm cell population from hPSCs optionally as defined above; (b) contacting the cardiovascular mesoderm cell population with a cardiovascular progenitor specification cocktail comprising an epicardial lineage promoting component under conditions suitable for the specification cocktail to penetrate the cardiovascular mesoderm cell population and culturing the contacted cardiovascular mesoderm cell population for a period of time sufficient to generate a WT1+ cardiovascular progenitor cell population.

In an embodiment, the cardiovascular progenitor specification cocktail comprises an epicardial cell promoting component, optionally wherein the epicardial cell promoting component comprises BMP4 in a suitable concentration for promoting epicardial cell development.

In another embodiment, the epicardial cell-promoting component comprises BMP4 at a concentration of at least 1.25 ng/mL, at least 2.5 ng/mL, at least 5 ng/mL or at least 10 ng/mL.

In another embodiment, the epicardial cell promoting component further comprises a Wnt component, optionally CHIR99021.

In yet another embodiment, the epicardial cell promoting component comprises BMP4 and a Wnt component optionally CHIR 99021.

In another embodiment, the WT1+ cardiovascular progenitor cell population is contacted with a maturation cocktail comprising a VEGF component.

In another embodiment, the WT1+ cardiovascular progenitor population is contacted with the maturation cocktail for about 4 or more days, optionally about 5, about 9, about 15 or about 20 days to produce a maturation cocktail contacted WT1+ epicardial lineage cell population.

In another embodiment, the maturation cocktail contacted WT1+ epicardial lineage cell population is purified/isolated.

In another embodiment, the maturation cocktail contacted WT1+ epicardial lineage cell population is cultured to obtain a zona occludins 1 (ZO1)+WT1+ epicardial lineage cell population, optionally wherein the ZO1+WT1+ epicardial lineage cell population is purified/isolated.

In another embodiment, the maturation cocktail contacted WT1+ epicardial lineage cell population and/or the ZO1+ WT1+ epicardial lineage cell population is contacted with an epithelial-to-mesenchymal transition (EMT) cocktail and cultured for a period of time.

In another embodiment, the EMT cocktail comprises: 1) a TGFβ component; 2) a TGFβ component and a FGF component, optionally wherein the TGFβ component and the FGF component are sequentially administered; or 3) FGF component.

In an embodiment, the TGFb component is TGFb-1. In an embodiment, the FGF component is bFGF.

As shown in Example 2, treatment of WT1+ cells EMT cocktail comprising TGFb gives rise to functional smooth muscle cells and treatment of WT1+ cells with EMT cocktail comprising TGFb and bFGF gives rise to a higher percentage of smooth muscle cells.

In an embodiment, the WT1+ cells are contacted with EMT cocktail from about 1 day to up to 3 weeks, for example about 1 day, 2 days, 3 days, 4 days, 5 days, 6 days, 7 days, 8 days, 9 days or about 10 days or about 1 week, 2 weeks or weeks. For example where the EMT cocktail comprises components that are sequentially administered, each component can be administered for about 1 day, 2 days, 3 days, 4 days, 5 days, 6 days, 7 days, 8 days, 9 days or about 10 days, or about 1 week, about 2 weeks or about 3 weeks.

In an embodiment, the TGFb component is TGFβ-1 and the concentration is from about 0.25 ng/ml to about 10 ng/ml or any one 0.1 ng/ml increment between 0.25 ng/ml and 10 ng/ml. Comparable concentrations of other TGFb components that produce similar TGFb signaling pathway activation can be used.

In an embodiment, the FGF component is bFGF and the concentration is from about 1 ng/ml to about 50 ng/ml or any 1 ng/ml increment between 1 ng/ml and 50 ng/ml. Comparable concentrations of other FGF components that produce similar FGF signaling pathway activation can be used.

In yet another embodiment, the EMT cocktail is contacted with the WT1+ population of cells according to the following schedule: 1) TGFβ-1 (for example about 0.25 to about 10 ng/ml) for about four days followed by four days with no additional factor (TGFβ), 2) TGFβ-1 (for example about 0.25 to about 10 ng/ml) for about four days followed by about four days with bFGF (for example about 1 to about 50 ng/ml) (TGFβ+bFGF), or 3) bFGF (for example about 1 to about 50 ng/ml) for about eight days (bFGF).

In another embodiment, the EMT cocktail comprises: 1) TGFβ component; or 2) a TGFβ component and a FGF component; and the cell population is cultured for a period of time to produce expression of an EMT marker such as SNAI1 and/or SNAI2 (detectable for example by measuring SNAI1 and/or SNAI2 transcript expression levels), a mesenchymal marker such as vimentin and/or CD90 and/or a smooth muscle marker such as SMA, optionally measured by flow cytometry or expression of a smooth muscle gene optionally CNN1, MYH11, TAGLN and SMTN.

As demonstrated in Example 2, the smooth muscle-like cells generated following EMT exhibited NE and PE induced calcium transients. The proportion of cells displaying calcium transients was highest (70%) in the population induced by TGFβ+bFGF indicating that this combination of signaling pathways efficiently promoted the development of smooth muscle cells capable of contraction (FIG. 16a). In an embodiment, the cell population is cultured for a period of time sufficient to produce a population of cells wherein at least 50%, at least 60% or at least 70% of the cells of the population display a calcium transient upon NE or PE stimulation.

In another embodiment, the population of cells is cultured until the population of cells expresses a smooth muscle marker or transcript to obtain a vascular smooth muscle lineage cell population, optionally until the population of cells expresses increased levels of a mesenchymal marker, optionally vimentin and/or CD90.

In another embodiment, the EMT cocktail comprises: an FGF component and the cell population is cultured to produce a fibroblast lineage cell population expressing an epicardial-derived fibroblast marker optionally TCF21, optionally measured by qRT-PCR.

It is further demonstrated in Example 2, that EMT induced hPSC-derived Epi cells can acquire invasiveness. For example invasion was monitored eight days following the induction of EMT and cells induced with bFGF alone were the most migratory and invaded the matrigel to the greatest depth. bFGF treatment also led to an increase in total cell number within the regions of interest (ROI; e.g. a region where the recording took place). Accordingly, in another embodiment, the cell population is cultured for a period of time sufficient to produce a population of cells wherein a proportion of the cells of the population acquire invasiveness. Invasiveness includes for example a cell that can migrate at least 100 μm, 150 μm, 200 μm, 250 μm, 300 μm, 400 μm, 500 μm or 600 μm in a Matrigel assay as described in Example 2.

In an embodiment, a cell population is purified/isolated optionally using flow cytometry, including fluorescence-activated cell sorting (FACS), magnetic separation, affinity chromatography, immunostaining and/or resistance to cytotoxic agent. In other embodiment, purification/isolation is based on detecting non-surface expressed markers, which can be achieved my monitoring an aliquot for example by quantitative RT or other PCR and immuno-based assays such as western blot.

In another embodiment, the population of cells is cultured to express TCF21 to obtain a fibroblast lineage cell population.

In another embodiment, the maturation cocktail contacted WT1+ epicardial lineage cell population and/or the WT1+ ZO1+ epicardial lineage cell population is cultured for a period of time to obtain a retinol dehydrogenase expressing epicardial lineage cell population, optionally wherein the retinol dehydrogenase expressing epicardial lineage cell population is ALDH1A2 expressing or Aldefluor positive staining, optionally wherein the cell population is at least 50% Aldefluor positive.

In another embodiment, the vascular smooth muscle lineage cell population, a fibroblast lineage cell population and/or a retinol dehydrogenase expressing epicardial lineage cell population is purified/isolated.

In another embodiment, the cardiovascular progenitor specification cocktail further comprises an activin/nodal inhibitor, optionally SB431542. For example, SB431542 added during the cardiovascular specification stage can promote both cardiomyocyte and epicardial specification.

In another embodiment, the PSCs are a human PSC. In yet another embodiment, the PSC is an induced pluripotent stem cell (iPSC) line, optionally a human iPSC and/or an embryonic stem cell (ESC) line, optionally a human ESC (hESC). In an embodiment, the iPSC is a fibroblast derived iPSC line.

A further aspect includes a purified population of cardiovascular lineage cell or cell population and/or a cell or cell population differentiated therefrom produced according to the method of described herein. For example it is demonstrated here that cardiomyocyte or epicardial lineage cells can be specified with contaminating cell types. In an embodiment, the purified population is comprised in a gel, optionally Matrigel. Accordingly, the desired population can be purified with minimal intervention.

In an embodiment, the cells are adhered to a solid support such as a dish or flask.

Another aspect includes a composition comprising a purified/isolated cardiovascular lineage cell or cell population and/or a cell or cell population differentiated therefrom produced according to the method of described herein; and a suitable diluent.

A suitable diluent includes for example a suitable culture medium, or freezing medium containing for example serum, a serum substitute or serum supplement and/or a suitable cryoprotectant such as dimethyl sulphoxide (DMSO), glycerol Methylcellulose or polyvinyl pyrrolidone.

Another aspect includes a culture medium supplement comprising a cardiovascular progenitor specification cocktail, optionally comprising a BMP component in a concentration for specifying cardiomyocytes or comprising a BMP component and a Wnt component for epicardial specification. The components can be in liquid or powder form for reconstitution.

The components can be comprised in a single supplement to be added to base media such as Life Technologies StemPro-34. The amount of the components in the supplement can for example be amounts that when diluted in a culture medium (e.g. when diluted in a 450 mL base medium) result in concentrations described herein.

Another aspect includes a culture medium comprising the specification cocktail optionally comprising a BMP component in a concentration for specifying cardiomyocytes or comprising a BMP component and a Wnt component for epicardial specification. Typical culture medium components such as can also be included Also included in another aspect is a kit comprising: 1) an agent for measuring expression of a marker expressed on a cardiovascular lineage cell or cell differentiated therefrom the marker selected from KDR, PDGFRα, NKX2-5+, WT1, ZO1, EMT marker such as SNAI1 and/or SNAI2, a mesenchymal marker such as vimentin and/or CD90 and/or a smooth muscle marker such as SMA, a smooth muscle gene optionally CNN1, MYH11, TAGLN and SMTN, TCF21, retinol dehydrogenase, and/or Aldefluor activity; and/or 2) a component or composition such as a culture medium comprising said component for inducing differentiation of a cardiovascular lineage cell population, the components selected from cocktail optionally comprising a BMP component in a concentration for specifying cardiomyocytes or comprising a BMP component and a Wnt component for epicardial specification.

The agent can for example be an antibody or fragment thereof for immuno-assays and flow based methods, primers for detecting a particular transcript and/or a probe for detecting expression by a probe based method such as RT-PCR, qRT-PCR, in situ hybridization and Millipore SmartFlare.

The composition and kit components can include any of the components described elsewhere herein and optionally instructions for use. For example, in an embodiment, the kit comprises a supplement comprising components etc. to induce differentiation of one or more stages or lineages described herein (e.g. including components described in the Examples). In an embodiment, the kit comprises a base culture medium, optionally a base culture medium described herein and a culture medium supplement described herein.

The cells produced according to a method described herein can be used to screen for agents that promote and/or inhibit cardiovascular lineage cell differentiation.

Accordingly a further aspect includes a method for identifying a cardiovascular cell differentiation promotion agent comprising the steps: (a) contacting a test cell population with a test agent at a step in a method described herein; (b) monitoring for expression of a marker selected from KDR, PDGFRalpha, NKX2-5+, WT1, ZO1, a mesenchymal marker such as vimentin and/or CD90 and/or a smooth muscle marker such as SMA, a smooth muscle gene optionally CNN1, MYH11, TAGLN and SMTN, TCF21, retinol dehydrogenase, and/or Aldefluor activity levels in the test cell population and a control; and (c) identifying the test agent as a cardiovascular cell differentiating promotion agent when the test agent induces and/or increases expression of the cardiovascular marker and/or induces specification of cardiomyocyte, epicardial or EPDC.

For example, co-culture assays can be performed in which hPSC-derived epicardium and cardiomyocytes can be mixed and plated either in aggregate or monolayer format. After a pre-determined amount of time, cultures may be assayed by qRT-PCR, flow cytometry, or immuno-based methods for changes in gene and protein expression. Cultures can be assessed for example for sarcomere morphology by staining for alpha actinin, atrial natriuretic factor (ANF), and/or brain natriuretic peptide (BNP); mitochondrial maturity which can for example be assessed using flow cytometry and/or immunological methods; myosin regulatory light chain 7 (MYL7) which is predominantly expressed in adult atrial muscle and/or WT1 downregulation (e.g. indicative of epicardial maturity). Examples of flow cytometry and immunological methods are provided in the Examples.

In an embodiment, the method is used for drug screening of a cardiovascular drug, for example for promoting and/or interfering with cardiac and/or vascular remodeling.

In an embodiment, HPSC derived cardiomyocyte and epicardial lineage cells and/or tissue produced using a method described herein are 1) co-cultured, optionally in combination with endothelial cells; 2) contacted with a test agent; and 3) assessed for i) cell death or ii) increased proliferation, optionally in endothelial cell numbers; and/or iii) altered tissue organization, compared to a control, wherein a decrease in cell death, an increase in proliferation one or more of the cell lineages and/or I) decreased or II) increased cellular organization compared to the control is indicative that the test agent is a putative cardiovascular drug. Endothelial cell numbers can for example be assessed by staining for CD31; cell death and/or proliferation can be assessed for example by flow cytometry, cell counting methods and/or flow cytometry; and cellular organization be assessed visually.

In an embodiment, the method is for identifying putative agents for promoting epicardium differentiation, replacement of scar tissue, revascularization of ischemic areas etc. In an embodiment, HPSC derived cardiomyocyte and epicardial lineage cells and/or tissue produced using a method described herein are 1) co-cultured, optionally in combination with endothelial cells; 2) contacted with a test agent under hypoxic or other cardiotoxic conditions; and 3) assessed for i) cell death or ii) increased proliferation, optionally in endothelial cell numbers; and/or iii) altered tissue organization under hypoxic conditions, compared to a control, wherein a decrease in cell death, an increase in proliferation one or more of the cell lineages and/or I) decreased or II) increased cellular organization compared to the control is indicative that the test agent is a putative agent for promoting epicardium differentiation, replacement of scar tissue, revascularization of ischemic areas. Endothelial cell numbers can for example be assessed by staining for CD31; cell death and/or proliferation can be assessed for example by flow cytometry, cell counting methods and/or flow cytometry; and cellular organization be assessed visually.

Myocardial infarction can also be induced a variety of model organisms and hPSC-derived epicardial cells can be transplanted to the outer lay of the heart. Heart function recovery, myocyte proliferation/survival, and the contribution of EPDCs can be assayed.

Accordingly a further aspect includes a method of introducing a cardiovascular population of cells into a subject in need thereof, comprising producing a population of cells according to a method described herein, purifying the cell population and administering said population of cells into the subject in need thereof.

The population of cells is optionally comprised is an isotonic composition suitable for administration to a subject.

A further aspect includes a method of treating a subject in need thereof, comprising transplanting to the subject a population of cells produced according to a method described herein, optionally a purified cell population.

In an embodiment, the subject has suffered or is suffering a transient ischemic attack. In an embodiment, the subject has ischemic heart diseases.

In an embodiment the subject is administered a population produced from hPSCs, wherein the hPSCs are autologous iPSCs.

A number of genes and gene products are described herein. All reference accession numbers for genes and gene products referred to, including TNNT2—NM_001276345.1, NKX2-5—NM_004387.3, WT1—NM_024426.4, TBX-18—NM_001080508.2, GATA4—NM_002052.3, GATA5—NM_080473.4, ISL1—NM_002202.2, TBX5—NM_000192.3, BNC1—NM_001717.3, ANXA8—NM_001271702.1, SNAI1—NM_005985.3, SNAI2—NM_003068.4, CCN1—NM_001299.4, MYH11—NM_001040113.1, TAGLN—NM_001001522.1, SMTN—NM_001207017.1, TCF21—NM_198392.2, ALDH1A1—NM_000689.4, ALDH1A2—NM_003888.3, and ALDH1A3—NM_000693.2, the sequences associated therewith are herein incorporated by reference in their entirely.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Media consisting of StemPro-34 (Life Technologies) supplemented with 10 ng/ml penicillin/streptomycin, 2 mM L-glutamine, 1 mM ascorbic acid, and 4 3 10_4 M monothioglycerol (MTG) (Sigma). Human-BMP4, human-bFGF, human-Activin A, human-DKK1, and human-VEGF (R&D Systems) were added at the indicated time points and concentrations. The Activin/Nodal/TGF-b and BMP inhibition experiments were carried out with SB-431542 (Tocris, Ellisville, Mo.) and dorsomorphin (Sigma), respectively. For experiments involving Wnt signaling, CHIR-99021 (Stemgent), XAV-939 (R&D), or IWP2(R&D) were used at the indicated concentrations. Cultures were maintained in a 5% $CO_2$, 5% $O_2$, 90% $N_2$ environment for the first 10-12 days and were then transferred into a 5% $CO_2$ air environment for the remainder of the culture period. At indicated time points, cells were harvested and analyzed by flow cytometry or cell sorted.

Results

Cardiomyocyte Specification.

Figure 1:
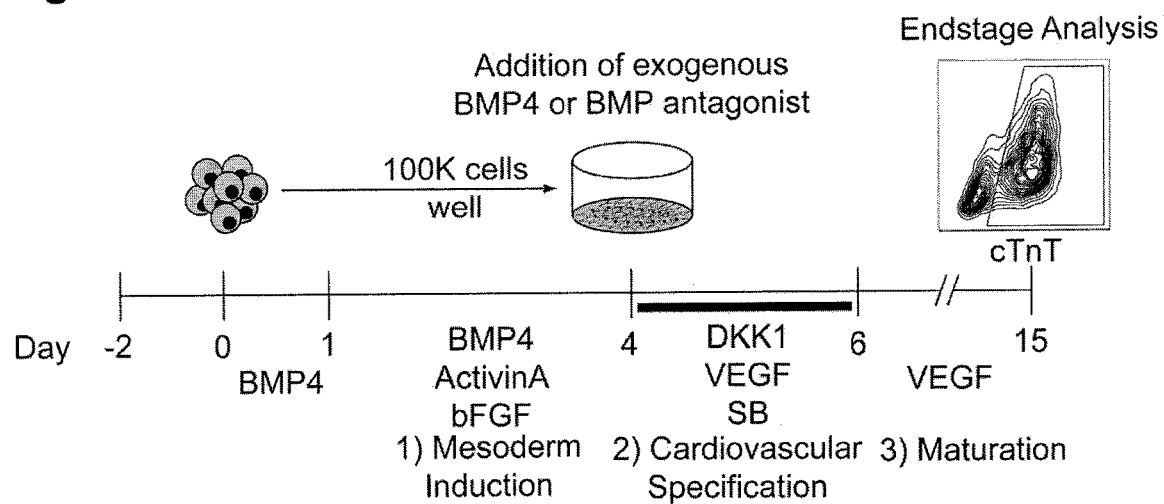
FIG. 1. Cardiomyocyte specification from hESCs. Scheme of the protocol used to differentiate hESCs towards the cardiomyocyte lineage highlighting the three main stages of development: 1) mesoderm induction, 2) cardiovascular specification and 3) maturation. Cells from ActivinA/BMP4-induced day 4 embryoid bodies (EBs) are plated as a monolayer on gelatin coated wells. The BMP pathway is manipulated for a 48-hour period (D4-D6) in the presence of VEGF (5 ng/ml), the Activin/Nodal (SB-431542 5.4 µM) and Wnt (DKK1 150 ng/ml) inhibitors. Following specification, the cultures were maintained in VEGF for 9 days and then analyzed for the presence of cTnT+ cardiomyocytes by flow cytometry.
Figure 2:
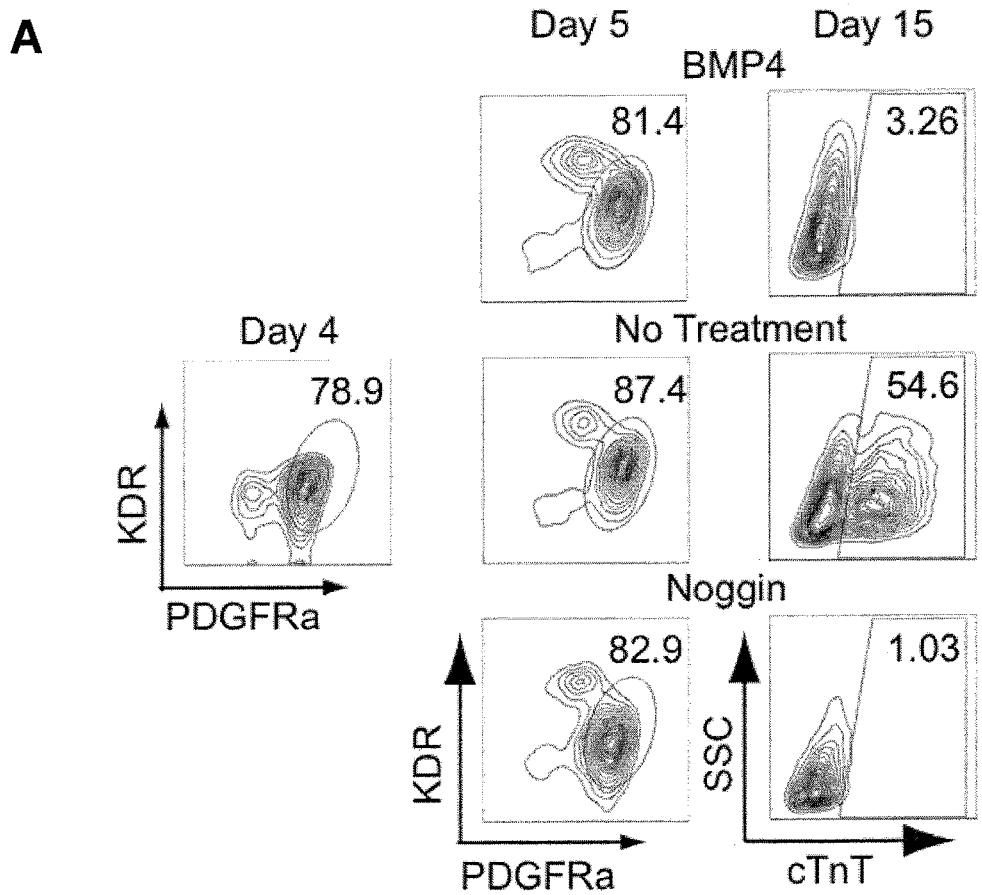
FIG. 2. BMP4 regulates the specification of cardiomyocytes from hESC-derived mesoderm. (a) Flow cytometric analyses showing the presence of the KDR+ and PDGFRα+ populations at day 4 and day 5 and the cTnT+ expression on day 15 of culture following no treatment (control), treatment with BMP4 (10 ng/ml) or the BMP inhibitor Noggin (400 ng/ml). (b) Total cell numbers per well at day 15 in the cultures treated as above. Error bars represent standard deviation from the mean from three experiments.
Figure 2:
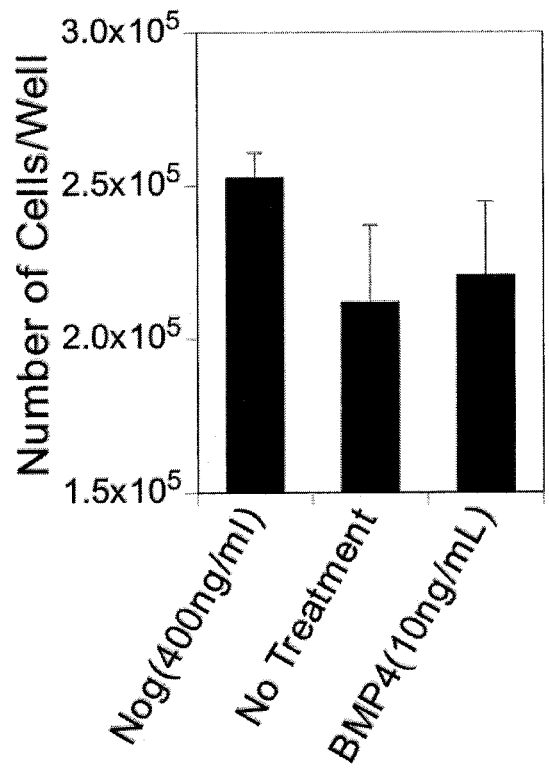

The development of the cardiovascular lineages from hPSCs progresses through at least three distinct steps, the induction of $KDR^+PDGFR^+$ cardiovascular mesoderm and the specification of this mesoderm to a cardiovascular fate resulting in the development of $NKX2-5^+$ cardiovascular progenitors and subsequently the maturation to contracting cardiomyocytes (FIG. 1). While activin A and BMP4 are the key regulators of the first stage[5] pathways controlling cardiac specification are less well understood and likely to differ from the induction step. To investigate the specification step, a model was established that enabled us to easily manipulate signaling pathways during this stage of development (FIG. 1). With this approach, cardiovascular mesoderm is induced in EBs with optimal concentrations of activin and BMP4 as described[5]. At day 4 of mesoderm induction, the EBs are dissociated, the cells plated in monolayer in microtitre wells ($1\times10^5$ per well) and treated with different pathway agonists and antagonists for 24-48 hours. Following this specification step, the cultures are maintained in the presence of VEGF and analyzed at day 15 for the presence of contracting cells that express cardiac troponin T (cTnT) and/or SIRPA. Initial studies showed that cardiomyocytes routinely develop in the presence of the Wnt inhibitor DKK1 and the activin/nodal/TGFβ inhibitor SB431542 indicating that these pathways are not required for specification. BMP signaling, on the other hand, had a profound effect at this stage, as addition of high levels of BMP4 or the inhibitors noggin or dorsomorphin completely blocked cardiomyocyte development (FIG. 2a). Neither manipulation dramatically impacted mesoderm development, although noggin did decrease the levels of KDR to some extent. Inhibition of cardiomyocyte development was not due to dramatic cell death as cell numbers in each group following the 48-hour treatment were not significantly different (FIG. 2b).

C.2. Generation of Epicardial Cells.

Figure 3:
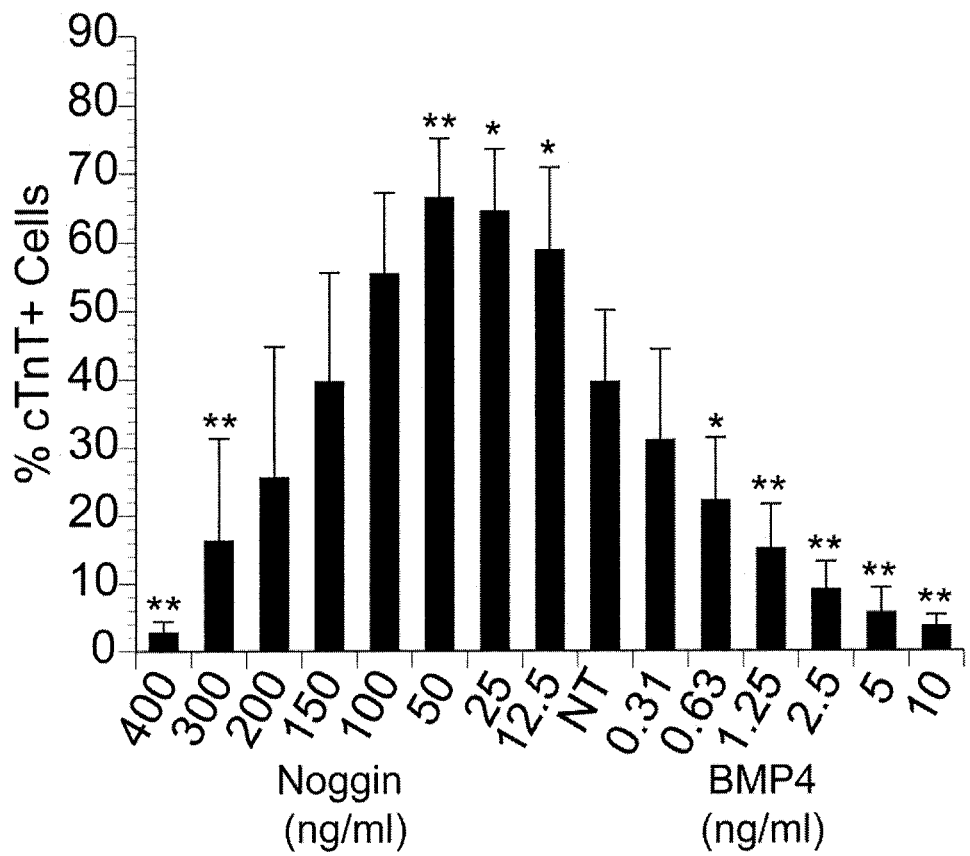
FIG. 3. BMP signaling dose-dependently specifies cardiomyocytes from hESC-derived mesoderm. Graphical representation of flow cytometry analyses indicating the percent cTnT+ cells in day 15 cultures generated from populations treated with the indicated amounts of BMP4 or Noggin. NT=no treatment. Bars represent standard deviation from the mean of the values from three independent experiments (N=3); *P≤0.05, **P≤0.01 when compared to no treatment.
Figure 4:
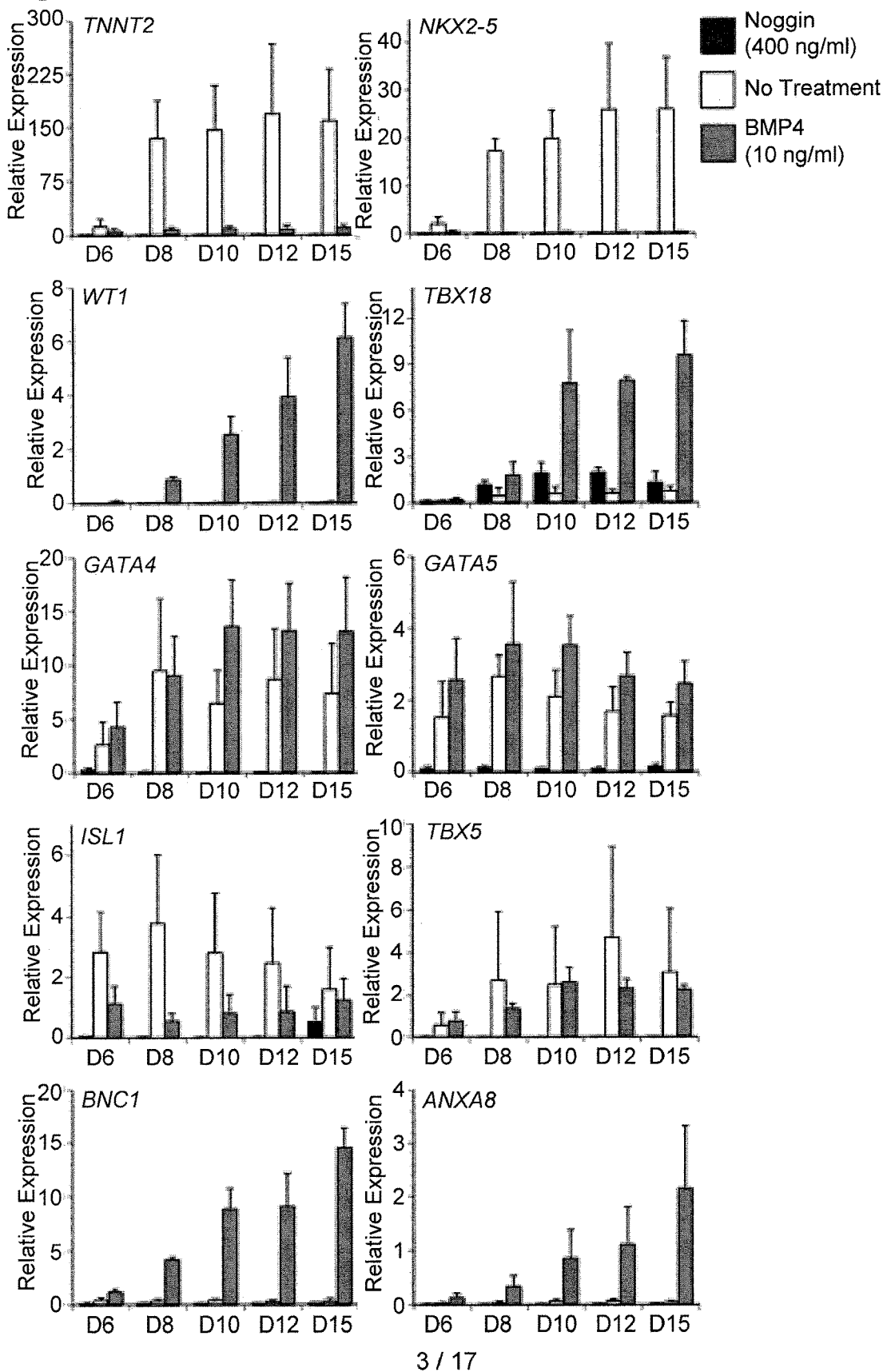
FIG. 4. qRT-PCR expression of myocardial and epicardial markers after BMP treatment. qRT-PCR-based expression of the indicated genes at days 6, 8, 10, 12, and 15 of culture in populations generated from no treatment (control), BMP4 treated or Noggin (400 ng/ml) treated cells. Values are relative to the housekeeping gene TBP. Error bars represent standard deviation from the mean of the values from three independent experiments (N=3); *P≤0.05, **P≤0.01 when compared to no treatment.
Figure 5:
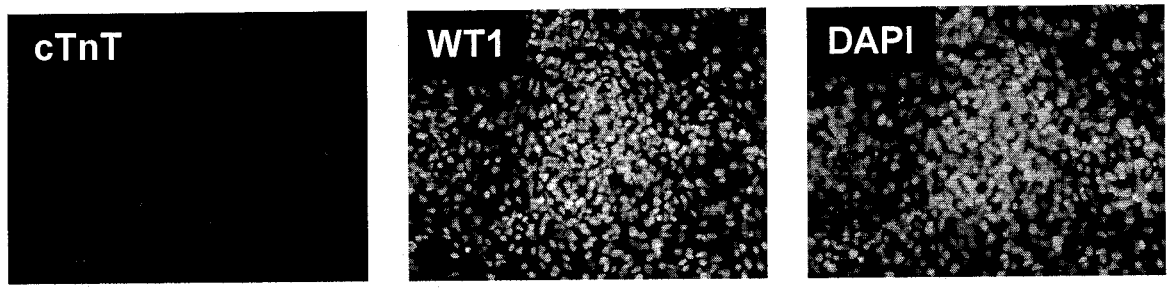
FIG. 5. BMP4-induced cells express the epicardial marker WT1.B Fluorescent immunostaining analyses showing the presence of cTnT and WT1 in no treatment (control), BMP4 (10 ng/ml) and Noggin (400 ng/ml) treated cells at day 15 of culture. DAPI staining shows cell nuclei FIG. 6. WT1+ epicardium generate epithelial sheets following passage. (a) Phase contrast microscopy and fluorescent immunostaining showing the morphology of the BMP4 (10 ng/ml) treated epicardial cells and the presence of ZO1 and WT1 at day 15 of culture. DAPI staining shows cell nuclei. Scale bar represents 100 µM. (b) Phase contrast microscopy and fluorescent immunostaining showing the morphology of the BMP4 (10 ng/ml) treated epicardial cells and the presence of ZO1 and WT1 4 days after passage (day 15+4). DAPI staining shows cell nuclei. Scale bar represents 100 µM.
Figure 5:
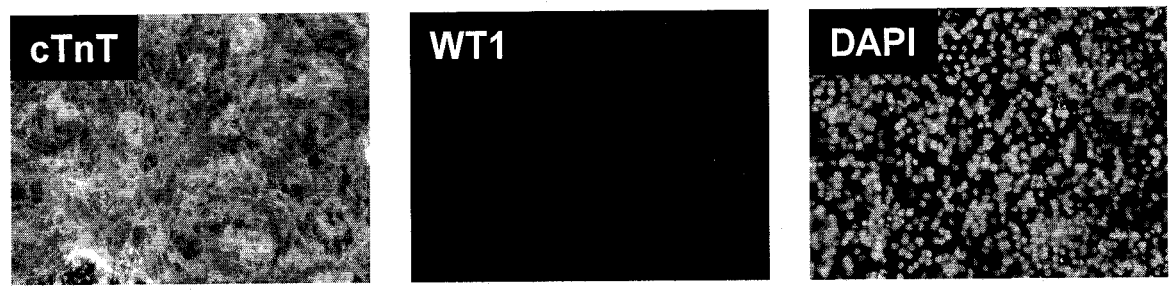
Figure 5:
Figure 6:
Figure 6:
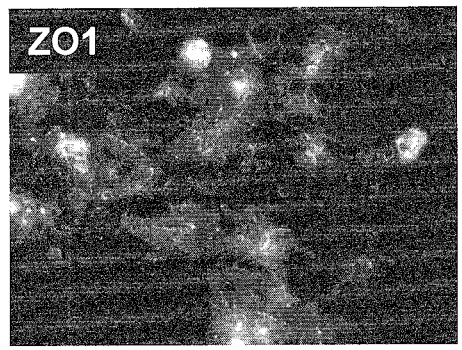
Figure 6:
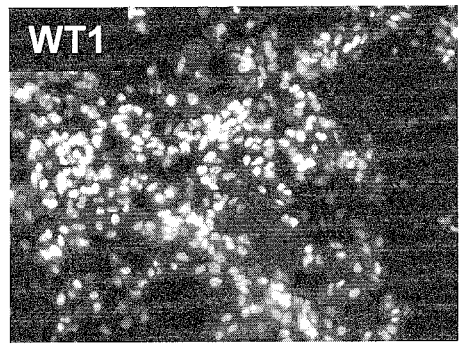
Figure 6:
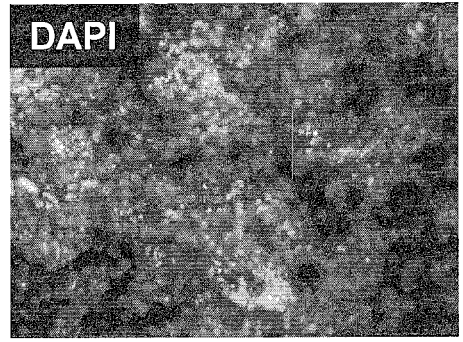
Figure 6:
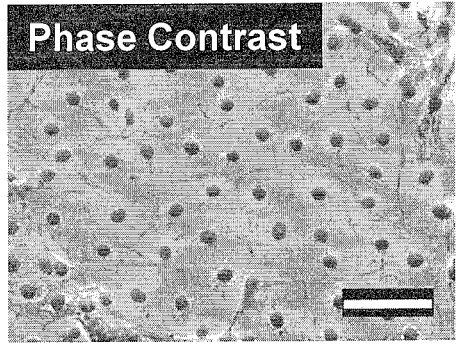
Figure 6:
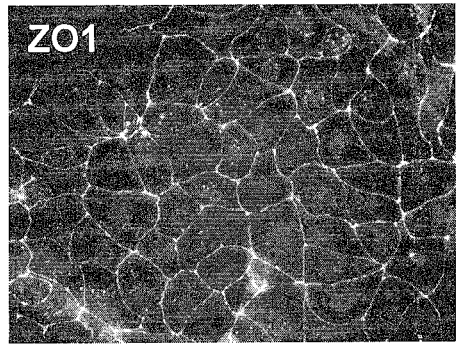
Figure 6:
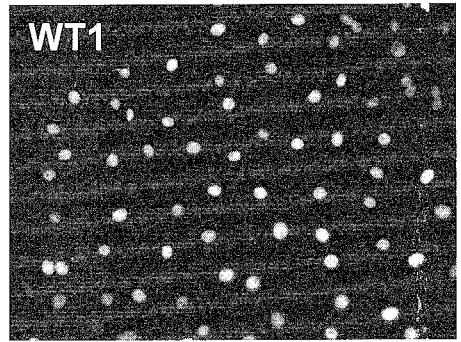
Figure 6:
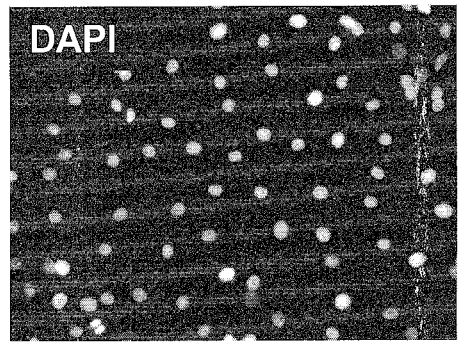

Titration of the agonist and antagonist during this specification step revealed that cardiomyocyte development requires low levels of BMP signaling, achieved by endogenous levels (produced by the differentiating cells) or through the addition of low levels of noggin (12.5-200 ng/ml) or low levels of BMP4 (0.31 ng/ml) (FIG. 3). High concentrations of noggin, as well as the addition of BMP4 at concentrations of 0.63 ng/ml or more, inhibited cardiomyocyte specification. As cell numbers in all groups were comparable (FIG. 2b), these observations suggest that other lineages are generated in the absence of signaling or in the presence of higher levels of signaling. As a first approach to identify these cells, we analyzed them for expression of a panel of myocardial and epicardial genes over a 6-15 day time course. As expected, genes indicative of cardiomyocyte development, including TNNT2 and NKX2-5 were only expressed in the control cultures (FIG. 4). Interestingly, two epicardial markers, WT1 and TBX18 were expressed exclusively (WT1) or predominantly (TBX18) in the cells generated from the BMP4 treated mesoderm, raising the possibility that they represent the developing epicardial lineage. Recently identified epicardial markers BNC1 and ANXA8[22] were also highly expressed in the BMP4-treated cells. Expression of other cardiac lineage markers including GATA4, GATA5, ISL1, and TBX5 were expressed, to some degree, in both the control and BMP4 treated cultures. The Noggin treated cultures did not express significant levels of any of these genes. Immunostaining revealed that WT1 (nuclear) was detected only in cells induced with BMP4, whereas cTnT was only present in cells of the non-treated group (FIG. 5), confirming the RT-qPCR analyses (FIG. 4). In vivo, the epicardial cells form an epithelial layer that surrounds the developing heart[18]. In addition to their distinct morphology, epithelial cells in culture are characterized by their ability to form tight junctions that can be monitored by the presence of the zona occludins 1 (ZO1) protein. At D15 of culture the WT1-expressing cultures did not show typical epithelial morphology and ZO1 expression was not observed (FIG. 6a). However, following passage and culture in a larger format (from a 96-well to a 6-well plate) for 4 days, WT1$^+$ cells expanded to generate a confluent monolayer with an epithelial morphology (FIG. 6b). Collectively, these observations strongly suggest that the BMP4-treated cells represent hPSC-derived epicardial (Epi) cells. In Zebrafish the BMP pathway has been observed to be essential for development of the PEO[23].

Figure 7:
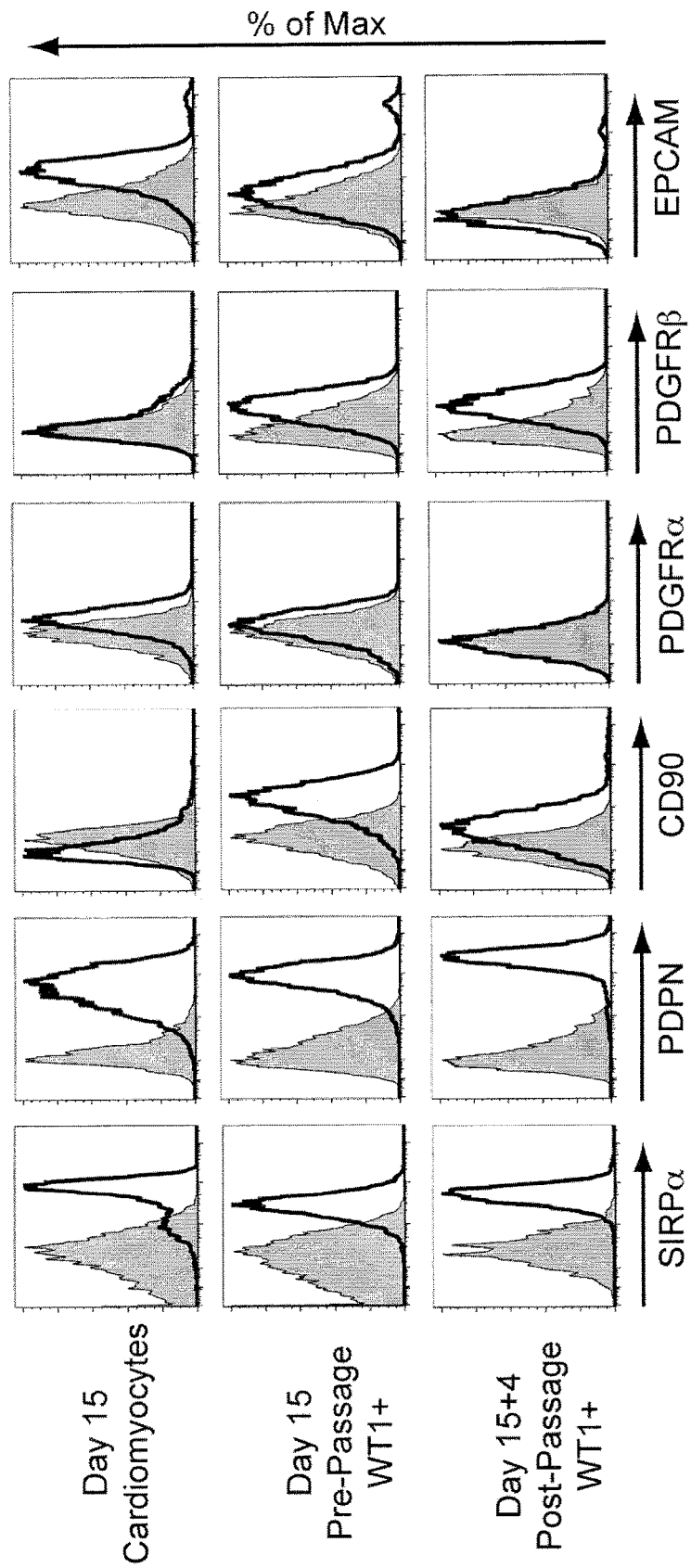
FIG. 7. Flow cytometry analysis for the expression of cell surface markers in day 15 cardiomyocytes, day 15 epicardium, and post-passage epicardium. Flow cytometric analyses of the indicated markers on day 15 cardiomyocytes, day 15 Epicardium and epicardium 4 days following passage (Day 15+4). Gray filled histogram indicates unstained fluorescence intensity.

To further characterize the WT1$^+$ Epi cells, both the day 15 and the passaged populations were analysed for expression of various surface antigens by flow cytometry. The expression patterns of these populations were compared to that of day 15 cardiomyocytes (FIG. 7). The cardiomyocytes and both WT1-expressing Epi populations stained positive for podoplanin (PDPN), a transmembrane glycoprotein found on developing mouse cardiomyocytes and on adult mouse epicardium[22, 24] and thought to be associated with cell migration. Interestingly, both Epi populations were also positive for SIRPα, a receptor previously shown to be expressed on hPSC-derived and fetal cardiomyocytes[8]. The WT1$^+$ Epi populations did express the mesenchymal/fibroblast marker CD90, although the levels were downregulated with passage. Consistent with our previous findings, cardiomyocytes did not express CD90[6]. PDGFRβ, expressed on embryonic epicardium in the mouse, was detected at low levels in both Epi populations[25]. In contrast, the mesoderm progenitor marker PDGFRα was not expressed on any of the populations, indicating that it is downregulated with lineage specification. The pan-epithelial marker EPCAM was present on the cardiomyocytes but not on either of the Epi populations. EPCAM expression is not reported as being expressed in the epicardium, most likely due to its simple squamous morpholohu[26, 27]. None of the populations expressed CD31, VE-Cadherin or cKIT indicating the lack of contaminating endothelial and hematopoietic cell types. Collectively, the findings from these flow cytometric analyses suggest that the Epi cells generated from mesoderm treatment with BMP phenotypically resemble the epicardium in the mouse.

Figure 8:
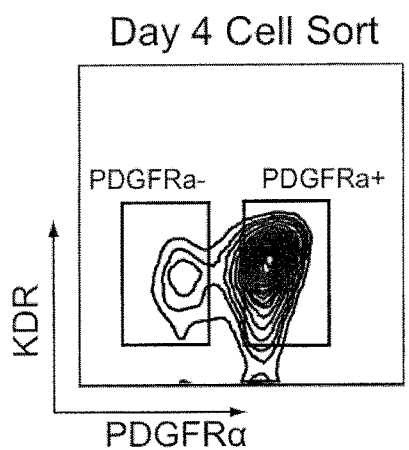
FIG. 8. Cardiomyocytes and epicardial cells are derived from day 4 PDGFRα+ mesoderm. (a) PDGFR+ and PDGFR− populations were isolated from day 4 EBs and the cells were plated under conditions that support cardiomyocyte or WT1+ cell development. (b) Flow cytometric analyses showing cTnT+ cells in day 15 cultures plated under pro-cardiogenic conditions. (c) Fluorescent immunostaining for the presence of WT1 positive cells in day 15 cultures plated under pro-epicardial inducing conditions (BMP4). DAPI staining shows the cell nuclei. (d) qRT-PCR-based expression analyses of the epicardial markers WT1 and TBX18 in the sorted populations at D15 following culture under pro-epicardial conditions. Values are fold change compared to the unsorted cultures. Error bars represent standard deviation the mean from the values from three independent experiments (N=3); *P≤0.05, **P≤0.01 from unsorted cultures.
Figure 8:
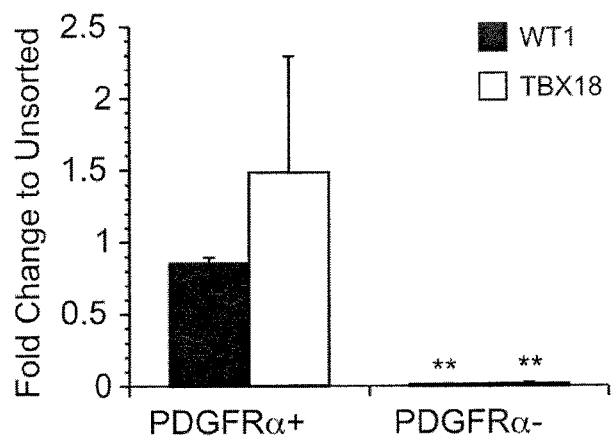
Figure 8:
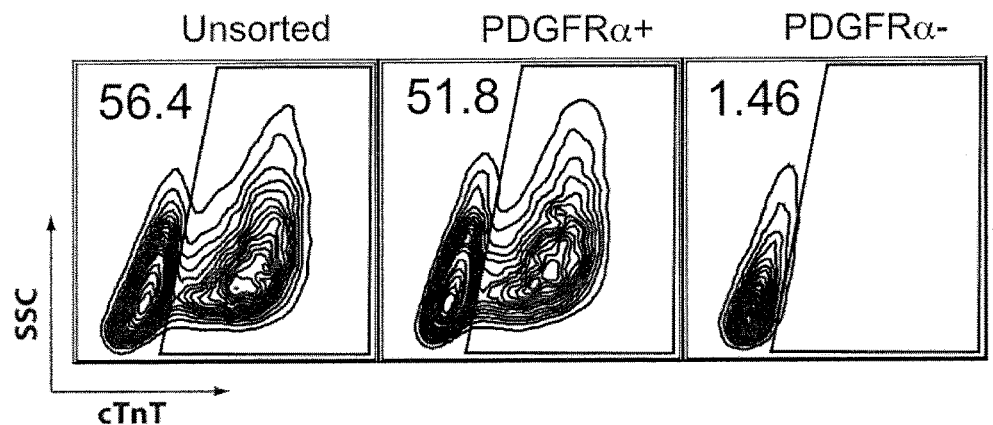
Figure 8:
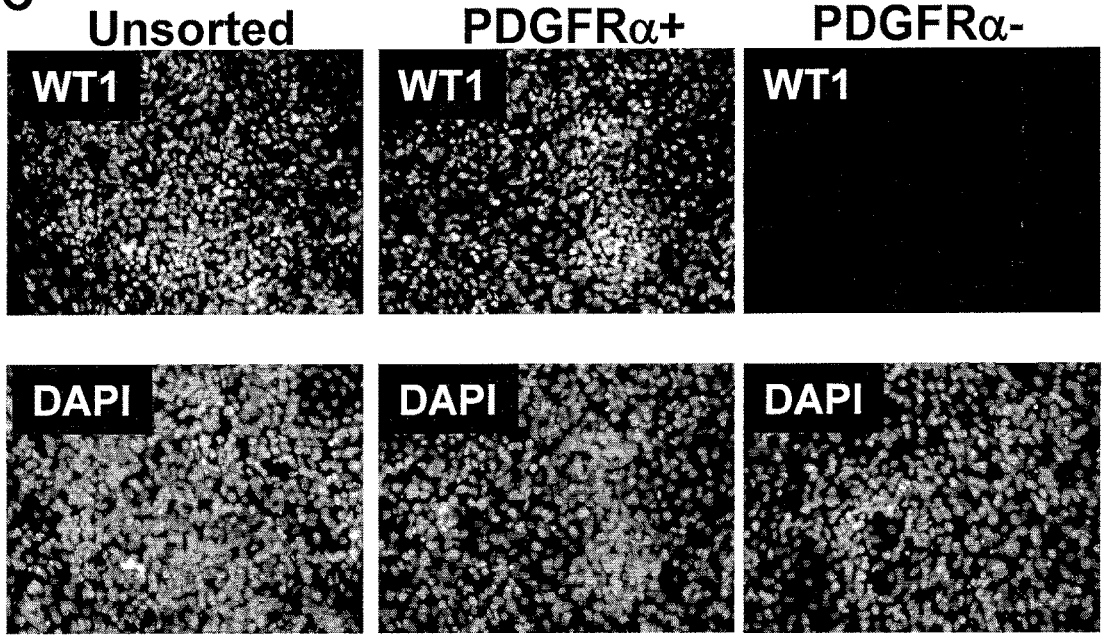

To demonstrate that the putative Epi cells are mesodermal origin, the PDGFRα$^+$ (mesoderm) and PDGFRα$^-$ (non-mesoderm) fractions from the day 4 populations were isolated and analyzed. As shown in FIG. 8, the cardiomyocytes (FIG. 7b) and the WT1$^+$TBX18$^+$ Epi cells (FIG. 7c,d) were generated only from the positive population indicating that they are of mesodermal origin. These observations represent the first demonstration that it is possible to generate epicardial cells from human pluripotent stem cells.

Figure 9:
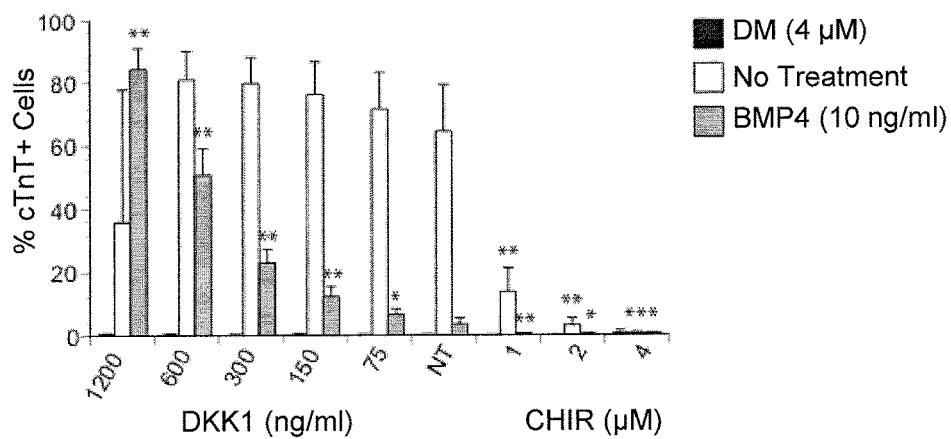
FIG. 9. BMP and Wnt signaling modulate cardiomyocyte and epicardial cell specification. (a) Graphical depiction of flow cytometric analyses showing the percent cTnT+ cells in day 15 cultures generated from untreated cells (control) or cells treated with either BMP4 (10 ng/ml) or the BMP inhibitor Dorsomorphin (DM 4 µM) in combination with the indicated amounts of DKK1 or CHIR. Error bars represent standard deviation from the mean of the values from three independent experiments (N=3); *P≤0.05, **P≤0.01 when compared to the 'no Wnt treatment' (NT) control in context of the indicated manipulation of the BMP pathway. (b) qRT-PCR-based analyses of WT1 expression on day 15 cultures generated from untreated cells (control) or cells treated with either BMP4 (10 ng/ml) or DM (4 µM) in combination with the indicated amounts of DKK or CHIR. Values are relative to the housekeeping gene TBP. Error bars represent standard deviation from the mean of the values from three independent experiments (N=3); *P≤0.05, **P≤0.01 when compared to the 'no Wnt treatment' (NT) control in the context of the indicated manipulation of the BMP pathway. (c) Flow cytometry analyses showing percent cTnT+ cells and qRT-PCR analyses for WT1 expression in day 15 cultures generated from untreated cells (control) or cells treated with either BMP4 (10 ng/ml) or DM (4 µM) in combination with the indicated amounts of XAV939 (XAV). Error bars represent standard deviation from the mean of the values from three independent experiments (N=3); *P≤0.05, **P≤0.01 when compared to no Wnt treatment (see FIGS. 9a and 9b) in the context of the specific BMP treatment. (d) Flow cytometry analyses showing percent cTnT+ cells and qRT-PCR analyses of WT1 expression in day 15 cultures generated from untreated cells (control) or cells treated with either BMP4 (10 ng/ml) or DM (4 µM) in combination with the indicated amounts of IWP2. Error bars represent standard deviation from the mean of the values from three independent experiments (N=3); *P≤0.05, **P≤0.01 when compared to no Wnt treatment (see FIGS. 9a and 9b) in the context of the specific BMP treatment.
Figure 9:
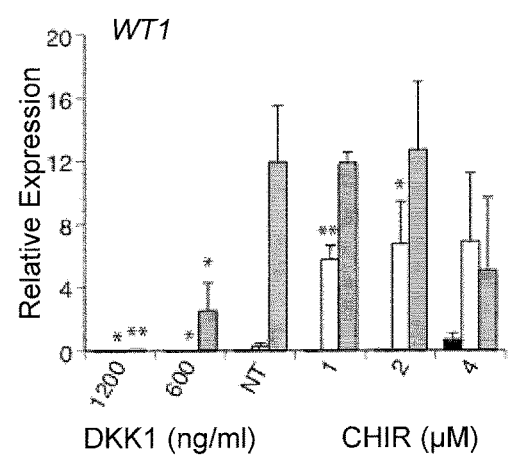
Figure 9:
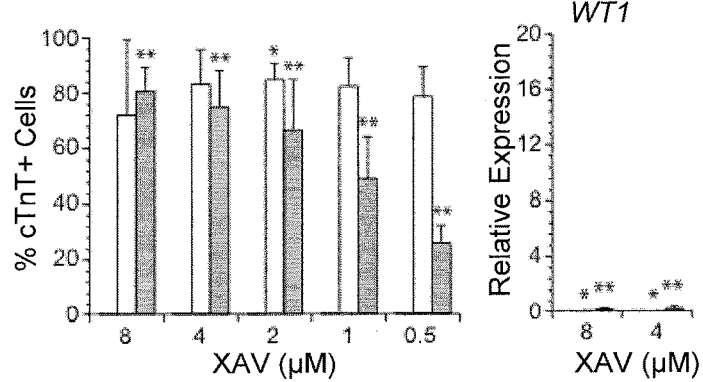
Figure 9:
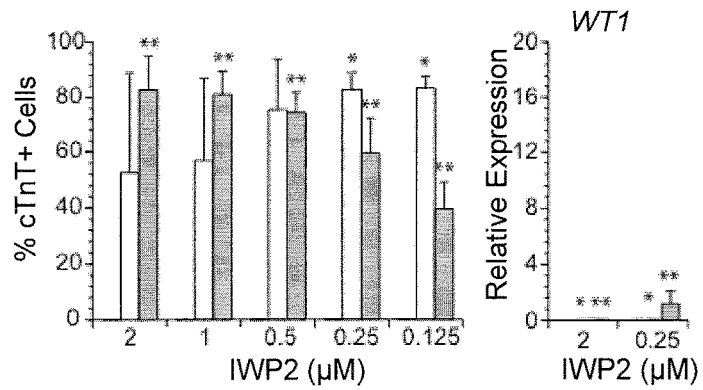

The findings that BMP4 can specify the cardiomyocyte and WT1$^+$ epicardial-like lineages in the presence of Wnt and activin/nodal inhibitors suggests that these pathways do not play a role at this stage of cardiovascular development. This interpretation, is not however, in line with the observations that the hearts of Dkk1$^{-/-}$Dkk2$^{-/-}$ null mice have an increased thickness of the epicardium and a decrease in the size of the myocardium compared to wild type littermates, suggesting that Wnt signaling does, in fact, play some role in the development of this lineage[28]. To reconcile these differences, Wnt signaling was further manipulated during stage 2, specifically focusing on inhibition of the pathway by titration of DKK1 or the small molecule antagonists XAV939 or IWP2 in the presence of either BMP4, the small molecule inhibitor of BMP dorsomorphin[29] (DM, in place of noggin) or no BMP pathway regulators control (no treatment). As shown in FIG. 9a, increasing amounts of DKK1 did alter the fate of the BMP4-treated cultures and promoted the development of cardiomyocytes rather than the WT1$^+$ Epi population. The addition of XAV939 or IWP2 had similar effects to that of high concentrations of DKK1 (FIGS. 9c and d). The cardiomyocyte potential of the DM-treated and non-BMP cultures were largely unaffected by these manipulations (FIGS. 9a, c and d). As expected, activation of the Wnt pathway by the addition of the small molecule Wnt agonist CHIR99021 (CHIR) inhibited cardiomyocyte development in the endogenous BMP control while DM-treated cultures were unaffected by CHIR addition (FIG. 9a).

Expression analysis showed that addition of higher concentrations of DKK1 or the small molecule antagonists XAV939 and IWP2 decreased WT1 expression in BMP4-treated cells indicating a loss of the epicardial population and instead specification of the cardiomyocyte lineage (FIG. 9b-d). Activation of the Wnt pathway by CHIR did not impact WT1 expression in BMP4-treated cells but did result in increased levels in the endogenous BMP population whereas DM treated cultures showed no change in WT1 expression (FIG. 9b). Taken together, these observations demonstrate that Wnt signaling is required for the specification of the epicardial lineage.

Figure 10:
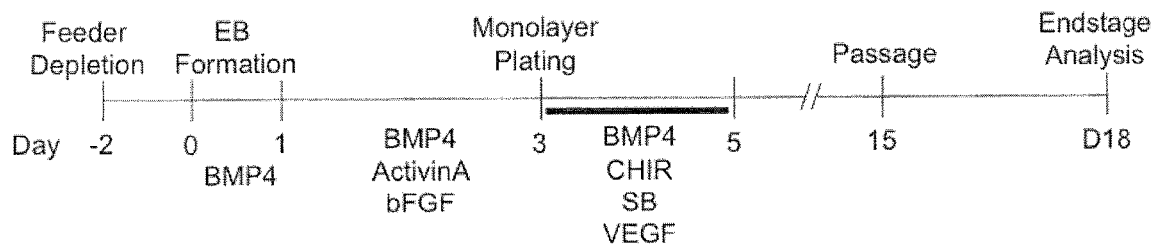
FIG. 10. Generation of WT1$^+$ epicardial cells from Sendai virus-derived hiPSCs and H7 hESCs. (a) Fluorescent immunostaining showing the expression of WT1 and ZO1 in a hiPSC-derived epicardial cultures. DAPI staining shows cell nuclei. Scheme indicates timing of manipulations and analysis. (b) Fluorescent immunostaining showing the expression of WT1 and ZO1 in a H7 hESC-derived epicardial cultures. DAPI staining shows cell nuclei. Scheme indicates timing of manipulations and analysis.
Figure 10:

For all remaining studies, cardiomyocytes were generated by the addition of BMP4 and XAV939 to the D4 mesoderm whereas the combination of BMP4 and CHIR was used to induce the WT1$^+$ epicardial lineage. Cells treated with the BMP inhibitor DM were used as the non-cardiomyocyte, non-epicardium control population. Using this protocol it was possible to generate WT1$^+$ epicardial-like cells from other hPSC lines including a human fibroblast-derived iPSC line (Sendai hiPSC) and the hESC line H7 (FIGS. 10a and b).

Figure 11:
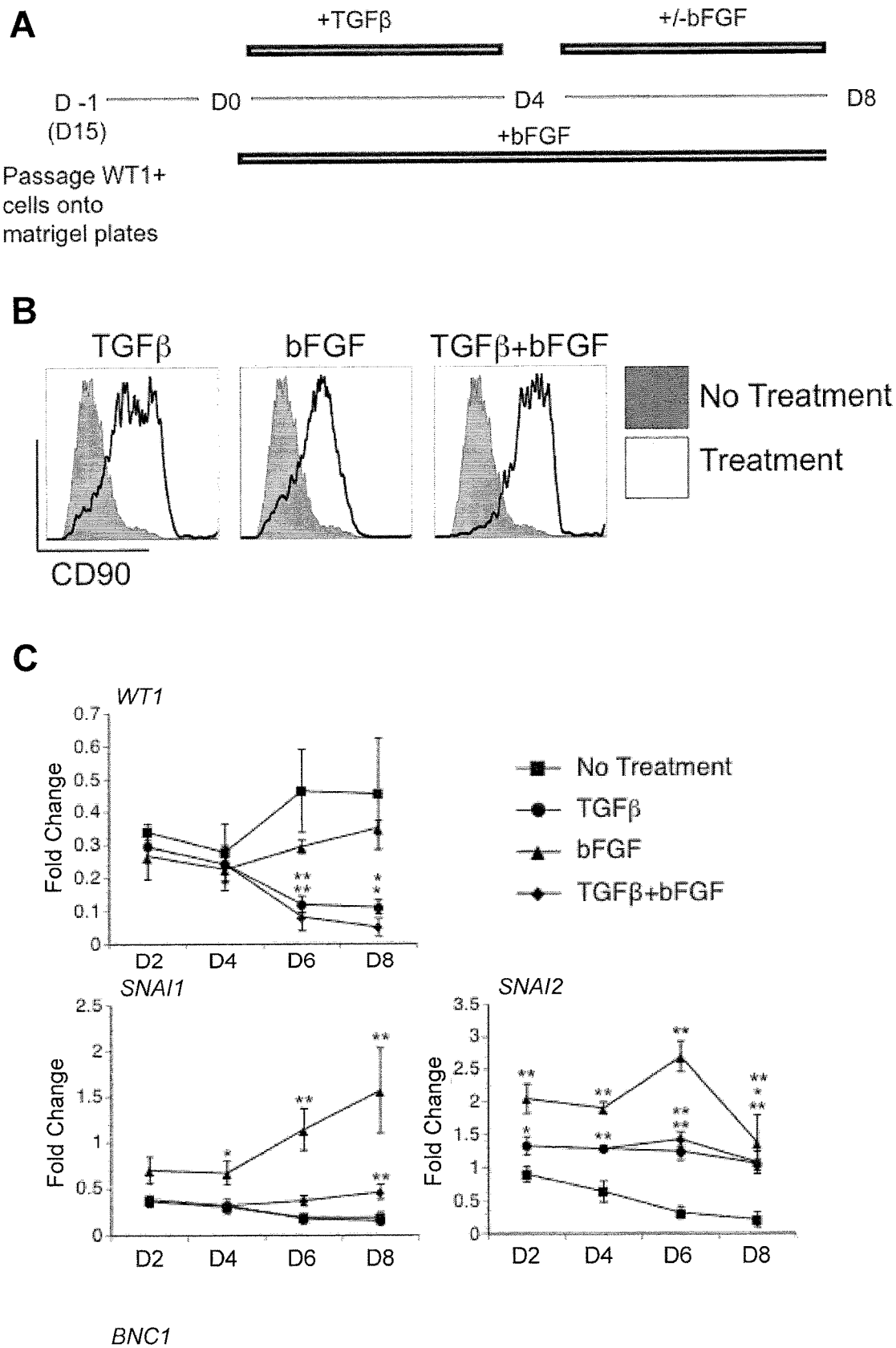
FIG. 11. WT1$^+$ epicardial cells undergo EMT in response to TGFβ1 and bFGF treatment. (a) Scheme of the protocol used for EMT induction. Day 15 WT1+ cultures are passaged, allowed to settle for 1 day and then treated with TGFβ1 (5 ng/ml) for 4 days followed by no treatment (TGFβ), sequential treatment with TGFµ1 (5 ng/ml) for 4 days followed by bFGF (10 ng/ml) for 4 days (TGFβ+ bFGF), or bFGF (10 ng/ml) treatment for 8 days (bFGF). No treatment of the cultures serves as a control. (b) Flow cytometric analyses of cultures 8 days following the initiation of EMT for the cell surface mesenchymal marker CD90. Gray filled histogram indicates control culture fluorescence intensity. (c) qRT-PCR-based expression of the epicardial gene WT1 and the EMT-induced genes SNAI1 and SNAI2 on days 2, 4, 6 and 8 after EMT initiation. Values are expressed as fold change to experiment-matched pre-passaged day 15 WT1+ cultures. Error bars represent standard deviation from the mean of the values from three independent experiments (N=3); *P≤0.05, **P≤0.01 compared to no treatment control.

To determine if the hESC-derived WT1$^+$ epicardial-like cells can undergo EMT, an assay was designed in which D15 epicardial cells are passaged, allowed one day to recover, and then treated for a total of eight days with one of four treatment regimens. The regimens consisted of: 1) TGFβ-1 for four days followed by four days with no additional factor (TGFβ), 2) TGFβ-1 for four days followed by four days with bFGF (TGFβ+bFGF), 3) bFGF for eight days (bFGF) or 4) no additional factors for eight days (FIG. 11a). Following culture under the different conditions, the cells were harvested and analyzed by qRT-PCR and flow cytometry.

Figure 12:
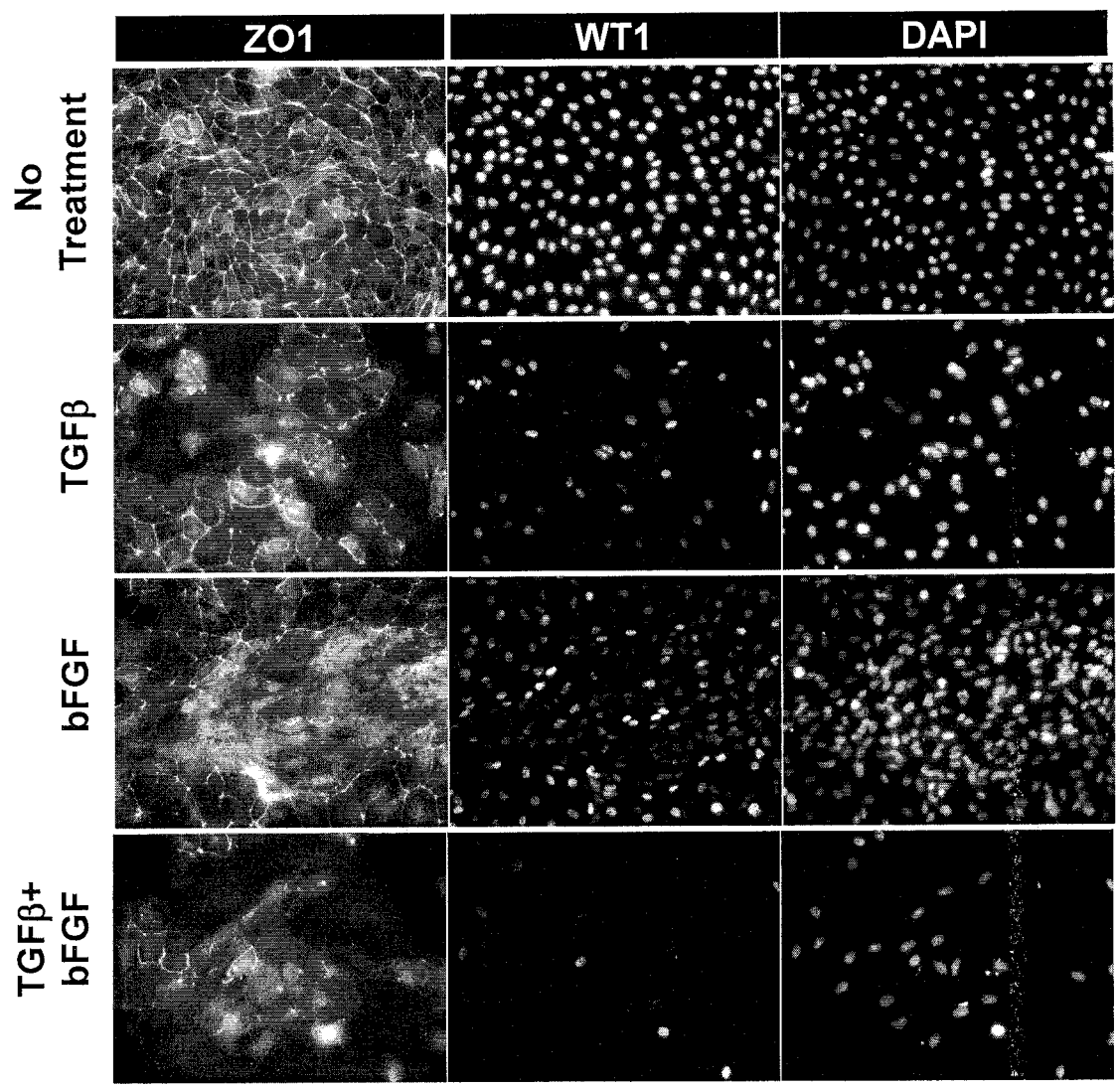
FIG. 12. WT1 and ZO1 expression is lost in response to EMT. Phase contrast and fluorescent immunostaining showing cell morphology and the expression of ZO1 and WT1 proteins in epicardial cultures 8 days after EMT initiation with the indicated factors. DAPI staining shows cell nuclei.

Expression levels of WT1 were downregulated immediately following passage and then gradually upregulated over the eight-day culture period (FIG. 11c). Cells treated with either TGFβ or TGFβ+bFGF showed steady decreases in WT1 expression over time, indicating a loss of epicardial identity (FIG. 11c). In contrast, the levels of WT1 expression did not decline below those of the control in the bFGF treated cells. Expression of the EMT markers SNAI1 and SNAI2 was also increased in the treated populations, although the levels varied depending on the cytokine combination. TGFβ, TGFβ+bFGF and bFGF all led to increases in SNAI2 expression while only bFGF induced the expression of SNAI1 (FIG. 11c). Immunostaining analyses illustrated that ZO1 expression was internalized or lost following TGFβ or bFGF treatment (FIG. 12). Expression of WT1 by immunostaining was consistent with transcript expression determined by qRT-PCR. The most significant loss of WT1 and ZO1 expression was observed in TGFβ+bFGF treated cells, although they were indistinguishable morphologically from those treated with only TGFβ. Flow cytometric analyses showed that cells in all treated groups had upregulated the mesenchymal marker CD90 compared to the untreated control (FIG. 11b), supporting the interpretation that TGFβ and bFGF had initiated EMT. Taken together, these findings indicate that the WT1$^+$ cells can undergo EMT following activation of the TGFβ and bFGF pathways and as such provide further evidence that they represent the in vitro equivalent of the developing epicardium.

Figure 13:
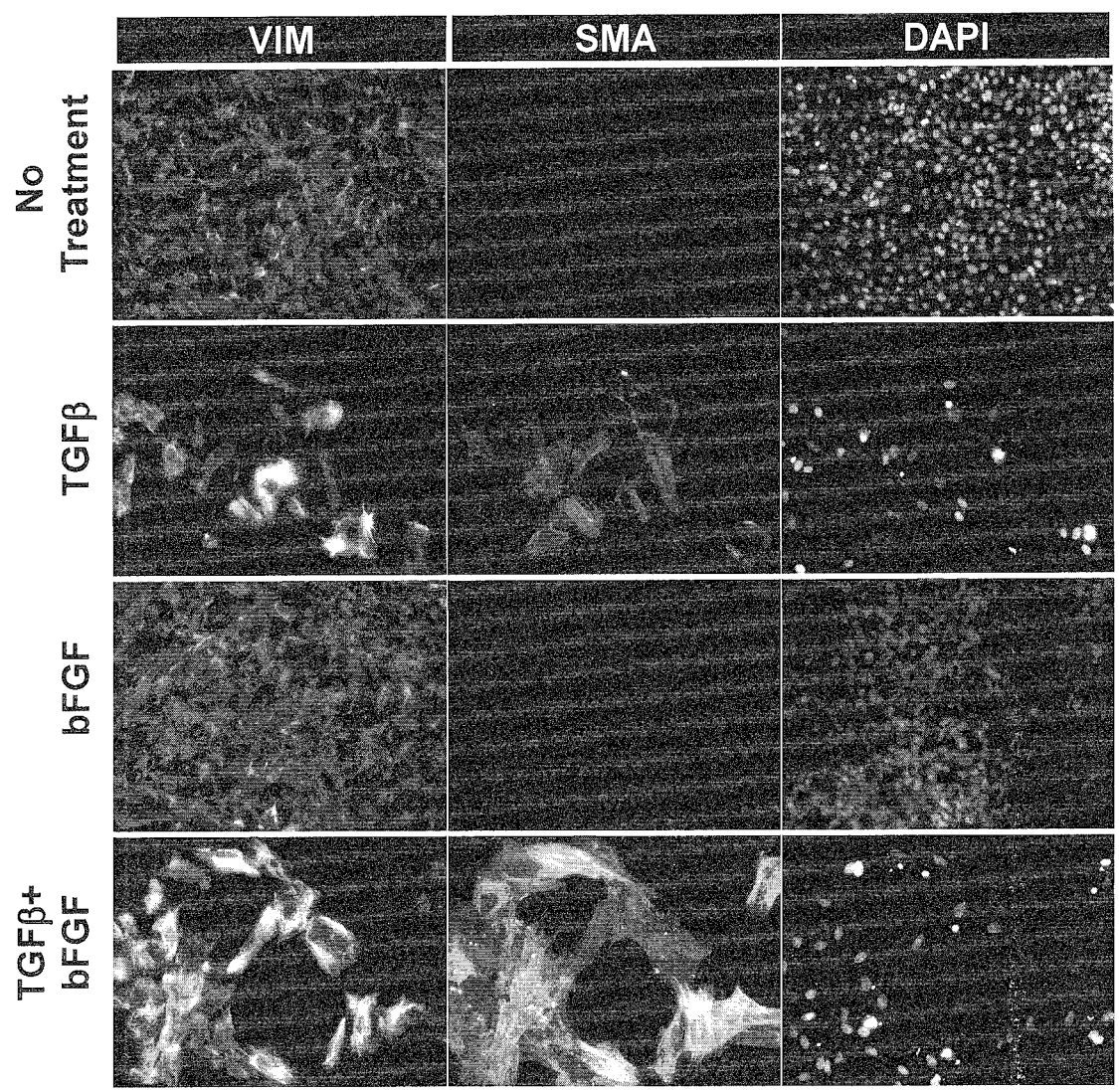
FIG. 13. EPDCs display characteristic expression of fibroblasts and vascular smooth muscle cell markers by fluorescent immunostaining. Fluorescent immunostaining showing α-Smooth muscle actin (SMA) and Vimentin (VIM) protein in cultures 8 days after EMT initiation with the indicated factors. DAPI staining shows cell nuclei.
Figure 14:
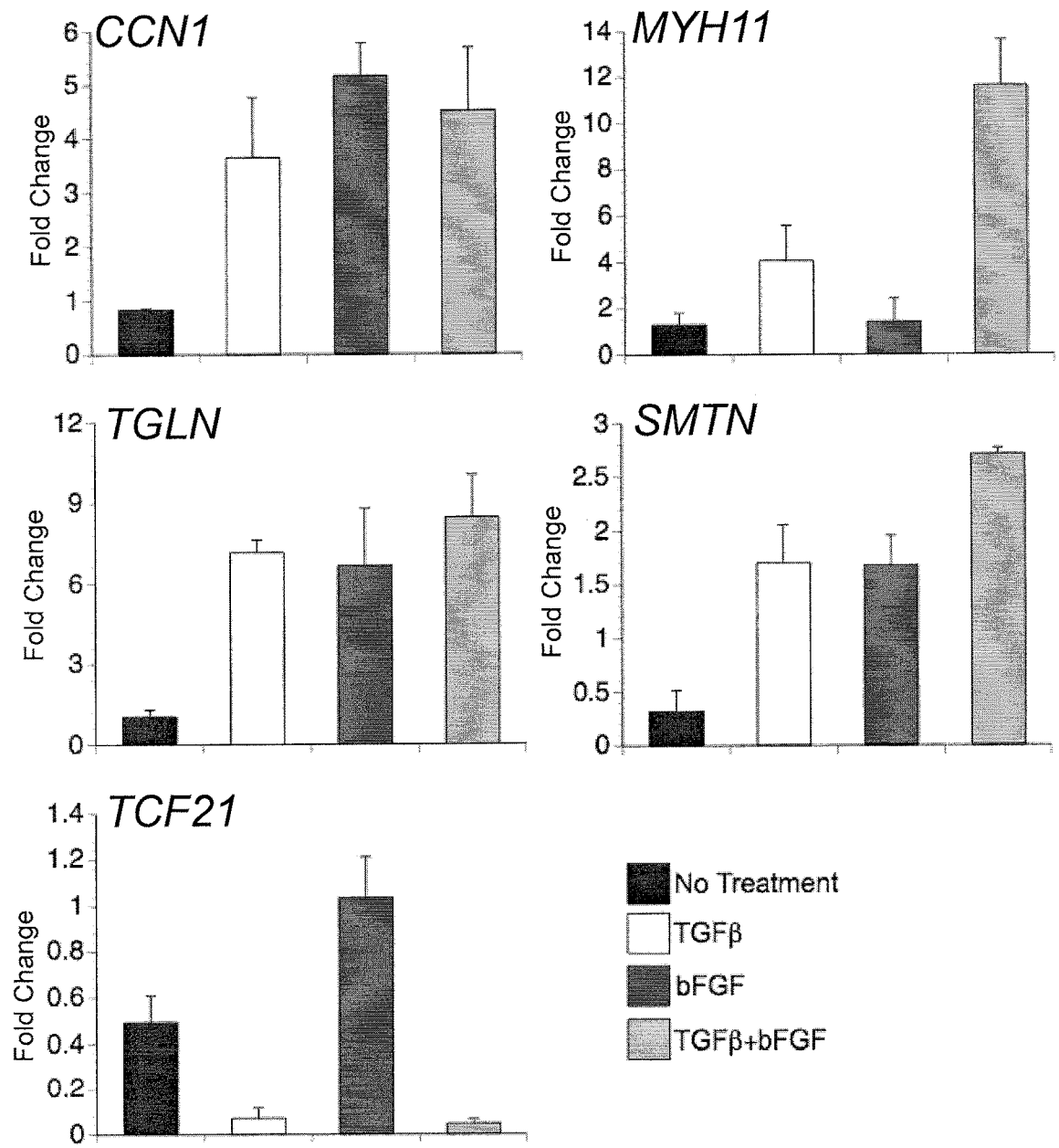
FIG. 14. EPDCs display characteristic expression of fibroblasts and vascular smooth muscle cell markers by qRT-PCR. qRT-PCR-based expression analyses of the smooth muscle genes CCN1, MYH11, TAGLN and SMTN and the epicardial/cardiac fibroblast gene TCF21 in the indicated cultures 8 days after EMT initiation. Values are expressed as fold change to experiment-matched pre-passaged day 15 WT1$^+$ epicardium cultures. Error bars represent standard deviation from the mean of the values from three independent experiments (N=3); *P≤0.05, **P≤0.01 compared to no treatment control cultures.

To identify the cell types being specified for during EMT induction, the derivative populations were analyzed for expression of the mesenchymal marker vimentin (VIM) and the smooth muscle marker α-smooth muscle actin (SMA) by immunostaining and for transcripts of the smooth muscle genes CNN1, MYH11, TAGLN and SMTN[30] and the epicardial-derived fibroblast marker TCF21[31] by qRT-PCR. While VIM was expressed to some degree in all populations, substantially brighter staining was observed in TGFβ and TGFβ+bFGF treated cells than in those treated with bFGF alone (FIG. 13). SMA was also detected at higher levels in the TGFβ and TGFβ+bFGF treated cells compared to those cultured with bFGF or in the absence of factors. These patterns suggest that cells treated with either TGFβ or TGFβ+bFGF are progressing along the vascular smooth muscle lineage. In support of this is the observation that cells treated with either TGFβ or TGFβ+bFGF upregulated expression of CNN1, MYH11, TAGLN and SMTN but not TCF21 (FIG. 14). In contrast, the bFGF induced population expressed TCF21 in addition to CNN1, TAGLN and SMTN (FIG. 14). These cells, however, did not express MYH11. Collectively, these findings indicate that TGFβ specifies hESC-derived WT1$^+$ epicardial cells towards a smooth muscle-like fate whereas bFGF promotes the development of fibroblast-like cells. bFGF treatment following TGFβ appeared to enhance the smooth muscle-like fate as observed by the increased expression of CNN1, MYH11, TAGLN and SMTN in these cells.

Figure 15:
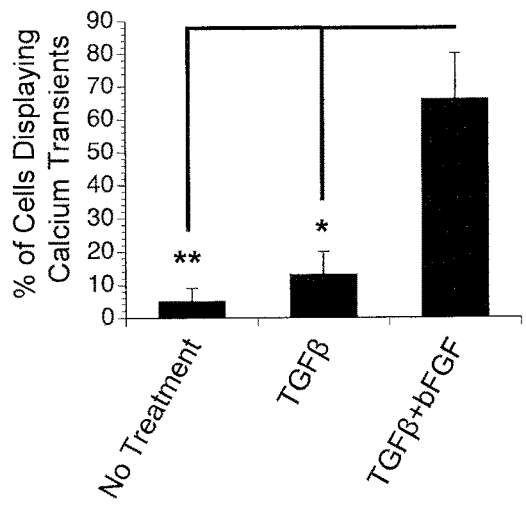
FIG. 15. hESC epicardial-derived smooth muscle-like cells generate action potentials when stimulated.
Figure 15:
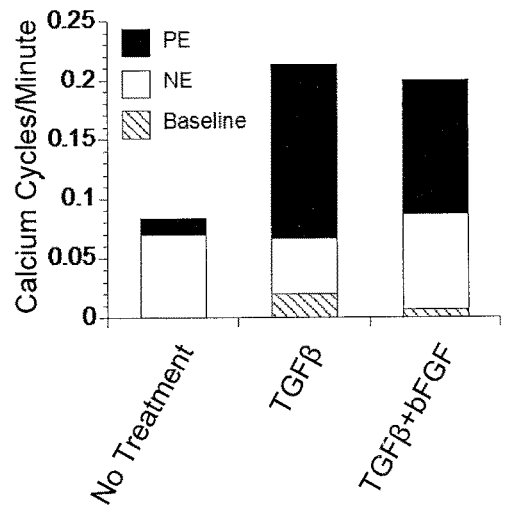
Figure 15:
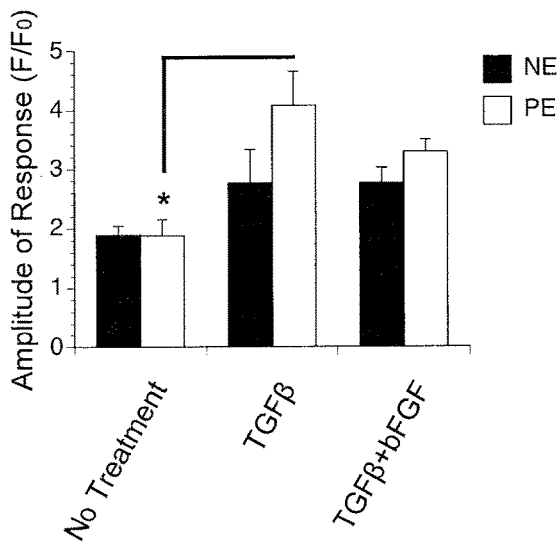
Figure 15:
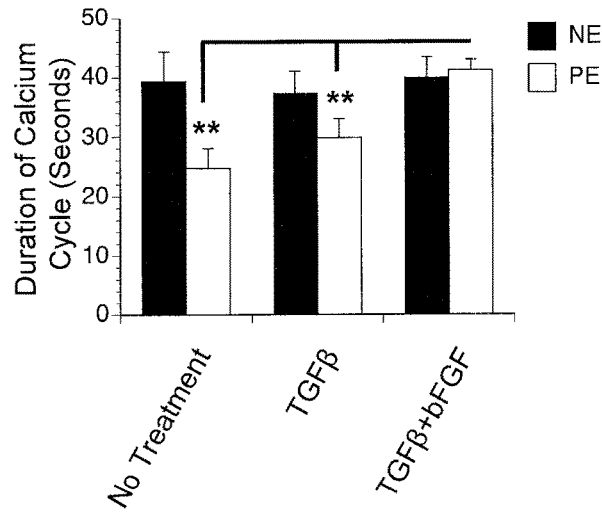

To test the contractile function of the smooth muscle-like cells generated following the EMT induced with TGFβ and TGFβ+bFGF, calcium transients were measured following stimulation with norepinephrine (NE) and phenylephrine (PE) using previously described methods[32]. The proportion of cells displaying calcium transients was highest (70%) in the population induced by TGFβ+bFGF indicating that this combination of signaling pathways efficiently promoted the development of smooth muscle cells capable of contraction (FIG. 15a). Of the cells that exhibited calcium transients, similar rates of cycling were observed in the TGFβ and TGFβ+bFGF induced cells following PE stimulation. Cells from both populations exhibited faster calcium cycling rates than those in the non-induced control cultures (FIG. 15b). The amplitude of calcium response was greatest in PE-treated TGFβ cells compared to control cultures (FIG. 15c). Finally, the duration of calcium transients following PE-treatment were significantly longer in the TGFB+bFGF induced cells than in those treated with TGFβ or those in the control population (FIG. 15d). Taken together these findings demonstrate that induction of the Epi cells with the combination of TGFβ+bFGF (or TGFb to a lesser extent) promotes the development of smooth muscle cells capable of responding to agonists that result in increased calcium handling that may facilitate smooth muscle action potentials and contractility.

It is well established that during heart development EPDCs, and in particular cardiac fibroblasts, invade the myocardial layer[33]. To assess this potential of the hPSC-derived Epi cells, their ability to invade a 3D layer of Matrigel following induction of EMT with the different factors was measured. To enable us to easily track the migration of the cells, the Epi population was generated from GFP expressing hESCs[48]. Matrigel invasion was monitored eight days following the induction of EMT by confocal microscopy and evaluated using 3D image reconstruction (FIG. 16a). The cells induced with bFGF alone were the most migratory and invaded the matrigel to the greatest depth (FIG. 16b), supporting the interpretation that they are fibroblastic in nature. Along with invasion, bFGF treatment also led to an increase in total cell number within the regions of interest (ROI). None of the other groups showed this expansion (no treatment, 73.8±6.1 cells per ROI; TGFβ, 56.8±9.5 cells per ROI; bFGF, 379.7±40.5 cells per ROI, p=0.0017; TGFβ+bFGF, 80.3±17.1 cells per ROI). Notably, the population induced with TGFβ alone showed little capacity to invade the Matrigel, even less than the non-treated control that may contain some cells that have undergone spontaneous EMT to the fibroblast lineage (white arrow heads). Cells induced with the combination of TGFβ+bFGF behaved similarly to the control population and were considerably less invasive than those induced with BFGF alone. To further quantify the degree of invasion, the proportion of cells in each population that migrated to different depths was calculated. Virtually all of the cells in the non-induced, the TGFβ-induced and TGFβ+bFGF-induced populations were detected within the first 200 µm of the gel. In contrast, approximately half of the cells in the bFGF-induced population migrated beyond this depth, some as far as 600 µm. Collectively, these findings demonstrate that the bFGF-induced population displays migratory behavior consistent with that predicted for EPDC in vivo. The observation that the cells with smooth muscle characteristics do not show this potential suggests that the maturation of this lineage likely occurs following migration into the tissue.

It is well accepted that the epicardium produces retinoic acid during development and following cardiac injury through the upregulation of the retinol dehydrogenase ALDH1A2. At D15 of differentiation the WT1$^+$ epicardial cells did not express ALDH1A2 (FIG. 15a), nor did they stain positive for Aldefluor by flow cytometry, a marker of aldehyde dehydrogenase activity (FIG. 15c). Following passage, however, the population showed steady increases in ALDH1A2 expression (FIGS. 15a and b). The retinol dehydrogenases ALDH1A1 and ALDH1A3, also involved in the synthesis of retinoic acid but not associated with the epicardium, were expressed only at low levels (FIG. 15a). Eight days following passage, the epicardial-like population had substantially upregulated aldehyde dehydrogenase activity as measured by Aldefluor staining where greater than 78% of the cells were positive (FIG. 15d). Cultures in which EMT had been induced with TGFβ, bFGF or TGFβ+bFGF showed dramatically lower levels of ALDH1A2 expression and Aldefluor staining, consistent with the interpretation that they are no longer epicardial cells (FIG. 15b).

Taken together, these studies show that passaged WT1$^+$ epicardial cells have the ability to undergo EMT towards smooth muscle-like and fibroblast-like cells in response to TGF and bFGF signaling. In the absence of an EMT-inducing signal, WT$^+$ cells acquire an epithelial-like morphology and aldehyde dehydrogenase activity through the upregulation of ALDH1A2, indicating their ability to synthesize RA (FIG. 18).

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

CITATIONS FOR REFERENCES REFERRED TO IN THE SPECIFICATION

1. Murry, C. E. & Keller, G. Differentiation of embryonic stem cells to clinically relevant populations: lessons from embryonic development. *Cell* 132, 661-680 (2008).
2. Burridge, P. W., Keller, G., Gold, J. D. & Wu, J. C. Production of de novo cardiomyocytes: human pluripotent stem cell differentiation and direct reprogramming. *Cell stem cell* 10, 16-28 (2012).
3. Laflamme, M. A. et al. Cardiomyocytes derived from human embryonic stem cells in pro-survival factors enhance function of infarcted rat hearts. *Nature biotechnology* 25, 1015-1024 (2007).
4. Yang, L. et al. Human cardiovascular progenitor cells develop from a KDR+ embryonic-stem-cell-derived population. *Nature* 453, 524-528 (2008).
5. Kattman, S. J. et al. Stage-specific optimization of activin/nodal and BMP signaling promotes cardiac differentiation of mouse and human pluripotent stem cell lines. *Cell stem cell* 8, 228-240 (2011).
6. Dubois, N. C. et al. SIRPA is a specific cell-surface marker for isolating cardiomyocytes derived from human pluripotent stem cells. *Nature biotechnology* 29, 1011-1018 (2012).
7. Limana, F., Capogrossi, M. C. & Germani, A. The epicardium in cardiac repair: from the stem cell view. *Pharmacology & therapeutics* 129, 82-96 (2011).
8. Cai, C. L. et al. A myocardial lineage derives from Tbx18 epicardial cells. *Nature* 454, 104-108 (2008).
9. Zhou, B. et al. Epicardial progenitors contribute to the cardiomyocyte lineage in the developing heart. *Nature* 454, 109-113 (2008).
10. Christoffels, V. M. et al. Tbx18 and the fate of epicardial progenitors. *Nature* 458, E8-9; discussion E9-10 (2009).
11. Li, P. et al. IGF signaling directs ventricular cardiomyocyte proliferation during embryonic heart development. *Development* (Cambridge, England) 138, 1795-1805 (2011).
12. Brade, T. et al. Retinoic acid stimulates myocardial expansion by induction of hepatic erythropoietin which activates epicardial Igf2. *Development* (Cambridge, England) 138, 139-148 (2011).
13. Smart, N. et al. Thymosin beta-4 is essential for coronary vessel development and promotes neovascularization via adult epicardium. *Annals of the New York Academy of Sciences* 1112, 171-188 (2007).
14. Zhou, B. et al. Adult mouse epicardium modulates myocardial injury by secreting paracrine factors. *The Journal of clinical investigation* 121, 1894-1904 (2011).
15. Smart, N. et al. De novo cardiomyocytes from within the activated adult heart after injury. *Nature* 474, 640-644 (2011).
16. Grieskamp, T., Rudat, C., Ludtke, T. H., Norden, J. & Kispert, A. Notch signaling regulates smooth muscle differentiation of epicardium-derived cells. *Circulation research* 108, 813-823 (2011).
17. van Tuyn, J. et al. Epicardial cells of human adults can undergo an epithelial-to-mesenchymal transition and obtain characteristics of smooth muscle cells in vitro. *Stem cells* 25, 271-278 (2007).
18. Austin, A. F., Compton, L. A., Love, J. D., Brown, C. B. & Barnett, J. V. Primary and immortalized mouse epicardial cells undergo differentiation in response to TGFbeta. *Dev Dyn* 237, 366-376 (2008).
19. Compton, L. A., Potash, D. A., Mundell, N. A. & Barnett, J. V. Transforming growth factor-beta induces loss of epithelial character and smooth muscle cell differentiation in epicardial cells. *Developmental dynamics: an official publication of the American Association of Anatomists* 235, 82-93 (2006).
20. Smith, C. L., Baek, S. T., Sung, C. Y. & Tallquist, M. D. Epicardial-derived cell epithelial-to-mesenchymal transition and fate specification require PDGF receptor signaling. *Circ Res* 108, e15-26 (2011).
21. Weeke-Klimp, A. et al. Epicardium-derived cells enhance proliferation, cellular maturation and alignment of cardiomyocytes. *Journal of molecular and cellular cardiology* 49, 606-616 (2010).
22. Bochmann, L. et al. Reveaking new mouse epicardial cell markers through transcriptomics. *PloS one* 5, e11429 (2010).
23. Liu, J. & Stainier, D. Y. Tbx5 and Bmp signaling are essential for proepicardium specification in zebrafish. *Circulation Research* 106, 1818-1828 (2010).
24. Mahtab, E. A. et al. Cardiac malformations and myocardial abnormalities in podoplanin knockout mouse embryos: Correlation with abnormal epicardial development. *Dev Dyn* 237, 847-857 (2008).
25. Mellgren, A. M. et al. Platelet-derived growth factor receptor beta signaling is required for efficient epicardial cell migration and development of two distinct coronary vascular smooth muscle cell populations. *Circulation research* 103, 1393-1401 (2008).
26. Momburg, F., Moldenhauer, G., Hammerling, G. J. & Moller, P. Immunohistochemical study of the expression of a Mr 34,000 human epithelium-specific surface glycoprotein in normal and malignant tissues. *Cancer research* 47, 2883-2891 (1987).
27. Bumol, T. F., Marder, P., DeHerdt, S. V., Borowitz, M. J. & Apelgren, L. D. Characterization of the human tumor and normal tissue reactivity of the KS1/4 monoclonal antibody. *Hybridoma* 7, 407-415 (1988).
28. Phillips, M. D., Mukhopadhyay, M., Poscablo, C. & Westphal, H. Dkk1 and Dkk2 regulate epicardial specification during mouse heart development. *International journal of cardiology* 150, 186-192 (2011).
29. Yu, P. B. et al. Dorsomorphin inhibits BMP signals required for embryogenesis and iron metabolism. *Nature chemical biology* 4, 33-41 (2008).
30. Cheung, C., Bernardo, A. S., Trotter, M. W., Pedersen, R. A. & Sinha, S. Generation of human vascular smooth muscle subtypes provides insight into embryological origin-dependent disease susceptibility. *Nature biotechnology* 30, 165-173 (2012).
31. Acharya, A. et al. The bHLH transcription factor Tcf21 is required for lineage-specific EMT of cardiac fibroblast progenitors. *Development* (Cambridge, England) 139, 2139-2149 (2012).
32. El-Mounayri, O. et al. Serum-free differentiation of functional human coronary-like vascular smooth muscle cells from embryonic stem cells. *Cardiovascular research* 98, 125-135 (2013).
33. Lie-Venema, H. et al. Origin, fate, and function of epicardium-derived cells (EPDCs) in normal and abnormal cardiac development. *Scientific World Journal* 7, 1777-1798 (2007).

The invention claimed is:

1. A method of specifying a WT1+ cardiovascular progenitor cell population comprising the step of contacting an hPSC-derived KDR+ and PDGFRalpha+ cardiovascular mesoderm cell population with a cardiovascular progenitor specification cocktail comprising human BMP4 at a concentration of between 0.63 ng/ml and 10 ng/ml.

2. The method of claim 1, wherein the cardiovascular progenitor specification cocktail further comprises CHIR99021.

3. The method of claim 2, wherein CHIR99021 is present at a concentration of between 1 µM and 4 µM.

4. The method of claim 3, wherein the cardiovascular progenitor specification cocktail further comprises SB431542.

5. The method of claim 4, wherein the cardiovascular progenitor specification cocktail further comprises human VEGF.

6. The method of claim 5, wherein the human VEGF is present at a concentration of 5 ng/ml and the SB431542 is present at a concentration of 5.4 µM.

7. The method of claim 3, wherein the cardiovascular mesoderm cell population is contacted with the cardiovascular progenitor specification cocktail for at least 12 hours to about 48 hours.

8. The method of claim 1, wherein the hPSC-derived KDR+ and PDGFRalpha+ cardiovascular mesoderm cell population is dissociated prior to the step of contacting with the cardiovascular progenitor specification cocktail.

9. The method of claim 1, wherein the cardiovascular mesoderm cell population is contacted with the cardiovascular progenitor specification cocktail for at least 12 hours to about 48 hours.

10. The method of claim 9, wherein the BMP4 concentration in the cardiovascular progenitor specification cocktail is at least 1.25 ng/ml.

11. The method of claim 10, wherein the BMP4 concentration in the cardiovascular progenitor specification cocktail is 10 ng/ml.

12. A method of producing an epicardial lineage cell population comprising the step of contacting a WT1+ cardiovascular progenitor cell population with a maturation cocktail comprising suitable cell culture components in a suitable cell culture format for a period of from 2 to 20 days.

13. The method of claim 12, wherein the maturation cocktail further comprises VEGF.

14. The method of claim 13, wherein the contacting takes place for a period of from 2 to 9 days.

15. The method of claim 12, wherein the step of contacting takes place in a 96-well plate and, after 2-9 days, the cell population is passaged and cultured in a larger cell culture format than the 96-well-plate.

16. The method of claim 15, wherein the cell population is cultured in a larger cell culture format until they exhibit an epithelial morphology.

17. The method of claim 15, wherein the cell population is cultured in a larger cell culture format for 4 days.

18. The method of claim 15, wherein the larger cell culture format is a 6-well plate.

19. The method of claim 14 comprising contacting the WT1+ cardiovascular progenitor cell population with the maturation cocktail for 9 days, further comprising passaging the cells, then culturing the cells in a larger format in a suitable medium for one day, followed by one of the following regimens comprising the step or steps of:
   (a) causing the cells to progress toward a vascular smooth muscle-like fate by treating them with human TGFβ-1 for a period of time;
   (b) causing the cells to progress toward a vascular smooth muscle-like fate by treating them with human TGFβ-1 for a period of time, followed by treating them with human bFGF for a period of time;
   (c) causing the cells to progress toward a fibroblast-like fate by treating them with human bFGF.

20. The method of claim 19, wherein:
   step (a) is performed and the cells are treated with human TGFβ-1 at a concentration of 5 ng/ml for 4 days, or
   step (b) is performed and the cells are treated with human TGFβ-1 at a concentration of 5 ng/ml for 4 days followed by treatment of the cells with human bFGF at a concentration of 10 ng/ml for a period of 4 days, or step (c) is performed and the cells are treated with human bFGF at a concentration of 10 ng/ml for 8 days.

21. A method of preparing an epicardial lineage cell population and causing the population to further differentiate comprising the steps of:
  (a) specifying a WT1+ cardiovascular progenitor cell population by a method comprising contacting an hPSC-derived KDR+ and PDGFRalpha+ cardiovascular mesoderm cell population with a cardiovascular progenitor specification cocktail comprising human BMP4 at a concentration of between 0.63 ng/ml and 10 ng/ml;
  (b) contacting the WT1+ cardiovascular progenitor cell population with a maturation cocktail comprising suitable cell culture components in a suitable cell culture format for a period of from 2-20 days;
  (c) passaging the cell population, then culturing the cell population in a larger cell culture format in a suitable medium for one day, optionally followed by one of the following regimens comprising:
    (i) causing the cell population to progress toward a vascular smooth muscle-like fate by treating it with human TGFβ-1 for a period of time;
    (ii) causing the cell population to progress toward a vascular smooth muscle-like fate by treating it with human TGFβ-1 for a period of time, followed by treating it with human bFGF for a period of time;
    (iii) causing the cell population to progress toward a fibroblast-like fate by treating it with human bFGF.

22. The method of claim 21, wherein
  (i) is performed and the cells are treated with human TGFβ-1 at a concentration of 5 ng/ml for 4 days, or
  (ii) is performed and the cells are treated with human TGFβ-1 at a concentration of 5 ng/ml for 4 days followed by treatment of the cells with human bFGF at a concentration of 10 ng/ml for a period of 4 days, or
  (iii) is performed and the cells are treated with human bFGF at a concentration of 10 ng/ml for 8 days.

* * * * *